United States Patent
Akizuki et al.

(10) Patent No.: US 6,797,334 B2
(45) Date of Patent: Sep. 28, 2004

(54) METHOD FOR FORMING GAS CLUSTER AND METHOD FOR FORMING THIN FILM

(75) Inventors: Makoto Akizuki, Gifu (JP); Mitsuaki Harada, Gifu (JP); Satoru Ogasawara, Gifu (JP); Atsumasa Doi, Gifu (JP); Isao Yamada, Hyogo (JP); Jiro Matsuo, Kyoto (JP)

(73) Assignees: Research Development Corporation of Japan, Saitama (JP); Sanyo Electric Co., Ltd., Osaka (JP)

( * ) Notice: Subject to any disclaimer, the term of this patent is extended or adjusted under 35 U.S.C. 154(b) by 0 days.

(21) Appl. No.: 10/648,393

(22) Filed: Aug. 27, 2003

(65) Prior Publication Data

US 2004/0037970 A1 Feb. 26, 2004

Related U.S. Application Data

(63) Continuation of application No. 10/025,899, filed on Dec. 26, 2001, now abandoned, which is a continuation of application No. 09/799,681, filed on Mar. 7, 2001, now abandoned, which is a continuation of application No. 09/566,740, filed on May 9, 2000, now abandoned, which is a continuation of application No. 08/951,959, filed on Oct. 17, 1997, now abandoned, which is a continuation of application No. 08/650,905, filed on May 17, 1996, now abandoned.

(30) Foreign Application Priority Data

| May 19, 1995 | (JP) | ............................................. 7-121983 |
| Sep. 22, 1995 | (JP) | ............................................. 7-244957 |
| Mar. 21, 1996 | (JP) | ............................................. 8-064861 |

(51) Int. Cl.[7] ............................................. C23C 14/00

(52) U.S. Cl. ............. 427/523; 427/255.25; 427/255.29; 427/294; 427/421; 427/566; 427/569

(58) Field of Search ...................... 427/255.25, 255.29, 427/294, 421, 566, 569, 523

(56) References Cited

U.S. PATENT DOCUMENTS

| 4,066,527 A | 1/1978 | Takagi et al. |
| 4,624,859 A | 11/1986 | Akira et al. |
| 4,812,326 A | 3/1989 | Tsukazaki et al. |
| 4,882,023 A | 11/1989 | Wendman |
| 5,091,009 A | 2/1992 | Nogami et al. |

(List continued on next page.)

FOREIGN PATENT DOCUMENTS

| JP | 60-14440 | 1/1985 |
| JP | 4-354865 | 12/1992 |
| JP | 5-102083 | 4/1993 |
| JP | 6-224146 | 8/1994 |
| JP | 63-38232 | 2/1998 |

OTHER PUBLICATIONS

"New Horizons in Materials Processing With ICB", Isao Yamada, Proc. 14th Symp. on ISIAT '91, Tokyo, (1991), Ion Beam Engineering Experimental Laboratory, pp. 227–235, (no month avail).

(List continued on next page.)

*Primary Examiner*—Bernard Pianalto
(74) *Attorney, Agent, or Firm*—Wenderoth, Lind & Ponack LLP

(57) ABSTRACT

In order to deopsit a high-grade and extra-thin film without causing damage to the substrate at a relatively low temperature, the present invention provides a method for forming a cluster which is a lumpy group of atoms or molecules of a reactive substance at the room temperature under the atmospheric pressure, irradiating electrons onto clusters, irradiating the resulting cluster ions onto a substrate surface by accelerating by an acceleration voltage, and at the same time or alternately, irradiating one or more component gases of the deposit film onto the substrate surface, thereby depositing a thin film on the substrate surface through reaction.

14 Claims, 27 Drawing Sheets

U.S. PATENT DOCUMENTS

| | | |
|---|---|---|
| 5,110,435 A | 5/1992 | Haberland |
| 5,350,607 A | 9/1994 | Tyson et al. |
| 5,459,326 A | 10/1995 | Yamada |
| 5,527,731 A | 6/1996 | Yamamoto et al. |
| 5,561,326 A | 10/1996 | Ito et al. |

OTHER PUBLICATIONS

"Irradiation Effects of a Mass Analyzed Gas Cluster Ion Beam on Silicon Substrates", Y. Yamashita et al., Proc. 1st Meeting on IESI '92, Tokyo, Ion Beam Engineering Experimental Laboratory, pp. 247, 250, (no month avail.).

"Irradiation effects of gas–cluster $Co_2$ ion beams on Si", I, Yamada et al., Nuclear Instruments and Methods in Physics Research B74 (1993) pp. 341–346, (no month avail.).

"Surface modifcation with gas cluster ion beams", I. Yamada et al., Nuclear instruments and Methods in Physics Research B79 (1993) pp. 223–226, (no month avail.).

"A Method and apparatus for surface modification by gas-cluster ion impact", J.A. Northby et al., Nuclear Insruments and Methods in Physics Research B79 (1993) pp. 336–340.

"Cluster Formation in Expanding Supersonic Jets: Effect of Pressure, Temperature, Nozzle Size, and Test Gas", hagena et al., The Journal of Chemical Physics, vol. 56, No. 5, Mar. 1, 1972, pp. 1793–1802.

"Micromachining with cluster ions", Henkes et al., Vacuum/ vol. 39, No. 6, pp. 541–542, 1989, (no month avail).

METHOD FOR FORMING GAS CLUSTER AND METHOD FOR FORMING THIN FILM

This application is a continuation of Ser. No. 10/025,899, filed Dec. 26, 2001, abandoned which is a continuation of Ser. No. 09/799,681, filed Mar. 7, 2001, now abandoned which is a continuation of 09/566,740, filed May 9, 2000, abandoned which is a continuation of Ser. No. 08/951,959, filed Oct. 17, 1997, abandoned which is a continuation of Ser. No. 08/650,905, filed May 17, 1996, abandoned.

FIELED OF THE INVENTION

The present invention relates to a method for forming a gas cluster, ionization thereof, and a method for forming a thin film with this ion beam. More particularly, the present invention relates to a method for forming a thin film based on a gas cluster ion, which is a group of reactive substances liquid or gaseous at the room temperature, which is useful for manufacturing semiconductors and other electronic devices and for surface modification of functional materials.

PRIOR ART

Methods of modifying a surface or forming a thin film on a substrate surface by irradiating monatomic or monomolecular ions onto a substrate surface have conventionally been used in practice. Since it is difficult to obtain a beam having a practically sufficient density because of the space charge effect between ions with a low-energy ion irradiation in these methods, it is the usual practice to use a high incident energy of several keV.

However, in these conventional methods using ions having a high incident energy, it is difficult to avoid damages to the substrate surface to be treated, and deterioration of the substrate surface and thin film properties.

Conventionally available methods for depositing a thin film on a semiconductor substrate have included the vacuum CVD method and the plasma CVD method. The vacuum CVD method has however a problem in that a sufficient deposition rate cannot be obtained unless the substrate temperature is raised to over 400° C. Consequently, when depositing a thin film such as lead titanate zirconate (Pb(Zr, Ti)O$_3$) directly onto a silicon substrate, for example, Pb, Ti and Zr diffuse throughout the silicon substrate, resulting in deterioration of electric characteristics.

The plasma CVD method, known as a method for forming a thin film at a low temperature, is defective in that much impurities are mixed up, and ions damage the substrate surface, with difficulty of film thickness control of a produced extra-thin film, resulting in the impossibility to apply for an insulating film or a ferroelectric film requiring a high quality.

It has thus been difficult to obtain a high-grade ultra-thin film because the quality of a thin film has deteriorated according as the forming temperature of thin film has become lower in the conventional techniques.

Under these circumstances as described above, there has been a strong demand for development of a novel method permitting surface modification of a substrate and formation of a high-quality thin film at a lower temperature, or particularly at the room temperature without heating the substrate, as a basic technique directed toward progress of a more sophisticated electronics such as ULSI.

In this situation of technology, the present inventors have already proposed a method of forming a lumpy group of atoms or molecules from a gas-reactive substance gaseous at the room temperature under the atmospheric pressure and irradiating gas cluster ions generated by ionizing same onto a substrate surface.

This method permits cleaning and flattening of a substrate surface, as well as even formation of a thin film with a lower energy, and is therefore attracting the general attention as a technique for ultra-high-accuracy fine surface fabrication with the use of a low-energy beam hereafter.

In spite of the considerable potentiality of this cluster ion beam, however, the technique has just paved the way to development, and many problems are still left for future resolution, including, for example, restriction on the kind of gas component substances and applications thereof.

The present invention was developed in view of the circumstances as described above, and has an object to provide a novel method related with gas cluster ion beam, which permits formation of a high-quality thin film having a flat and smooth interface in a state free from damage to the substrate at a relatively low temperature, through further development of the gas cluster beam technique.

SUMMARY OF THE INVENTION

As means to solve the above-mentioned problems, the present invention provides a method for forming a gas cluster, which comprises the steps of mixing a substance liquid at the room temperature under the atmospheric pressure and a pressurized gas, and causing the resultant mixture to spout as a gas from a nozzle to generate a cluster which is a lumpy group of atoms or molecules (claims 1 to 6).

The present invention provides also a method for forming gas cluster ions, which comprises the step of ionizing the thus formed gas cluster (claims 7–8), and a method for forming a thin film, which comprises the step of irradiating the thus formed cluster ions onto a substrate surface, thereby forming a thin film (claims 9–10).

Furthermore, the present invention provides a method for forming a thin film, which comprises the steps of forming a cluster which is a lumpy group of atoms or molecules of a reactive substance gaseous at the room temperature, irradiating cluster ions ionized therefrom onto a substrate surface, and at the same time or alternately, irradiating a single, or a plurality of, component gas of a deposit film onto the substrate surface to cause reaction of the both, thereby depositing a thin film on the substrate surface (claims 11–14), a method for forming an oxygen-containing gas cluster, which comprises the step of causing an oxygen-containing pressurized gas mixed with a rare gas to spout from a nozzle to form a gas cluster (claims 15–16), a method for forming an oxygen-containing gas cluster ion resulting from ionization thereof (claim 17), and a method for forming a thin film, which comprises the step of irradiating this ion onto a substrate surface, thereby forming a thin film (claim 18).

DETAILED DESCRIPTION OF THE INVENTION

As described above, the present invention makes it possible:

1) to form a gas cluster from a substance liquid at the room temperature under the atmospheric pressure, to form a gas cluster ion through ionization thereof, and to form a thin film by means of this gas cluster ion;

2) to form a thin film through simultaneous or alternate irradiation of the gas cluster ion of a reactive substance liquid or gaseous at the room temperature under the atmospheric pressure and other deposit film components; and 3) to form a gas cluster and an ion thereof from a mixture of a rare gas and an oxygen-containing gas, and to form an oxide film from this ion.

In the case of the above-mentioned methods, applicable substances liquid at the room temperature under the atmospheric pressure include various inorganic and organic compounds, oxygen-containing compounds such as metal complexes and organic metal compounds, and applicable pressurized gases include inert gases and reactive gases.

The above-mentioned liquid substance may be a gaseous cluster by transporting same with an inert gas or a rare gas. More specifically, there has conventionally been known a method of producing a cluster by charging a solid material into a crucible and heating it to raise the steam pressure, and clusterization is possible by a similar method even for a liquid material. This method has however problems in that, in order to replenish raw materials, the vacuum unit must be released to the open air, and the cluster beam cannot be directed downward. In the present invention, the improvements are such that raw materials can be replenished outside the vacuum unit by using the method of bubbling with a carrier gas or the like, and the beam can be directed downward irrespective of the gravity. In addition, use of the method of the present invention brings about such effects as an increase in the cluster size and an increase in the cluster beam intensity. Because the amount of supplied condensed gas can be controlled with the amount of supplied carrier gas capable of being precisely controlled, beam intensity can be stabilized. It is also possible to form a cluster comprising a mixture of liquid and gaseous materials by using a reactive gas such as O$_2$ as a carrier gas.

A cluster can be generated from a substance gaseous at the room temperature under the atmospheric pressure by causing a pressurized gas to spout through an expansion-type nozzle into a vacuum unit. In all cases, the thus formed cluster can be ionized through irradiation of electron or the like.

Figure 1:
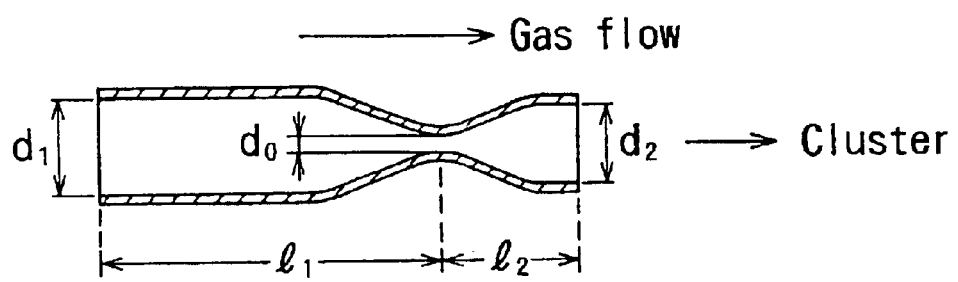
FIG. 1 shows a sectional view illustrating an expansion-type nozzle.

The size (lengths $l_1$ and $l_2$, and diameters $d_0$, $d_1$ and $d_2$) of the expansion-type nozzle may be appropriately determined in response to the amount of generated cluster, the substance to be formed into a cluster and distribution of cluster sizes, on the assumption of a circular nozzle having the shape shown in FIG. 1 as an example. The amount of generated cluster and the size distribution are dependent particularly on $l_2$ and $d_0$: a smaller $d_0$ and a longer $l_2$ correspond to a larger amount of generated cluster and a larger size. Typical values of $l_2$ and $d_0$ include approximately $l2=5–50$ mm, and $d0=0.02–0.2$ mm.

In the examples described later, the following values are employed, which may approximately be adopted:

$l_1=30$ mm, $l_2=32$ mm, $d_0=0.1$ mm, $d_1=12$ mm, $d_2=8$ mm.

The generated gas cluster is usually composed of from several tens to several thousand atomic or molecular groups. The extent of size of these groups may be determined, as described above, in response to the nozzle shape, the structure thereof, the gas supply pressure, and the kind of the substance to be treated.

Applicable reactive substances gaseous at the room temperature include, for example, oxides and carbides such as $CO_2$, $CO$, $O_2$, $N_2O$, $NO_x$, and $C_xH_yO_z$, nitrides such as $N_2$ and $NH_3$, $AsH_3$, $SiH_4$ and other reacting substances. Any of these substances may be used in mixture with a rare gas such as Ar and $H_2$.

In the case of $O_2$, mixture with a rare gas and further the use of a cooled expansion-type nozzle make it possible to form a gas cluster, to ionize same, and to form an oxide film through irradiation thereof onto a substrate.

As a component gas composing a deposit, such organic substance as an organic metal compound may be used in a gaseous form in response to the kind of the target deposit film. In this case, a rare gas capable of being supplied in the form of a halide, an alcoholate compound or a carbonyl compound of an element such as Ti, Zr, Pb or Nb may be used as a carrier.

These components may be supplied in the form of clusters.

The method for forming a thin film through a reaction between a reactive cluster ion beam and the substrate will now be described further in detail by means of examples.

EXAMPLE 1

Figure 2:
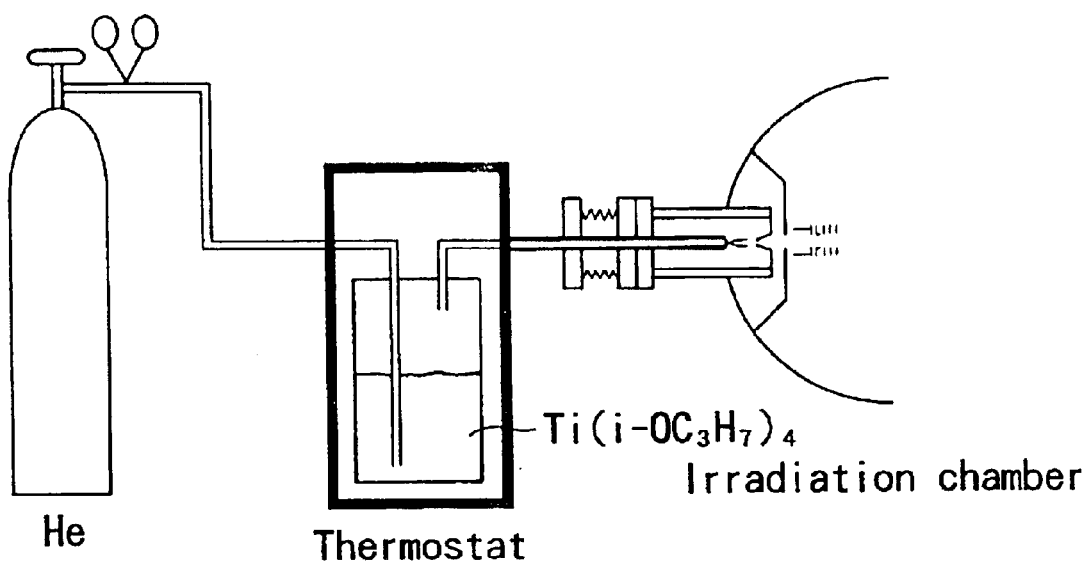
FIG. 2 shows a schematic view illustrating a system for generating gas clusters from a liquid substance.

FIG. 2 shows an example of the apparatus for generating a cluster by transporting vapor of a liquid material by means of a carrier gas and then causing same to spout from a nozzle. This demonstrates a case using tetraisopropoxytitanium ($Ti(i-OC_3H_7)_4$) liquid at the room temperature under the atmospheric pressure, in which temperature of a thermostat and a transport piping was raised to about 70 to 75° C. to increase the vapor pressure to about 1 Torr. He was employed as a carrier gas. Apart from this, a rare gas such as Ar or $H_2$ may be used. A material having a lighter weight results in generation of a cluster more efficiently.

Figure 3:
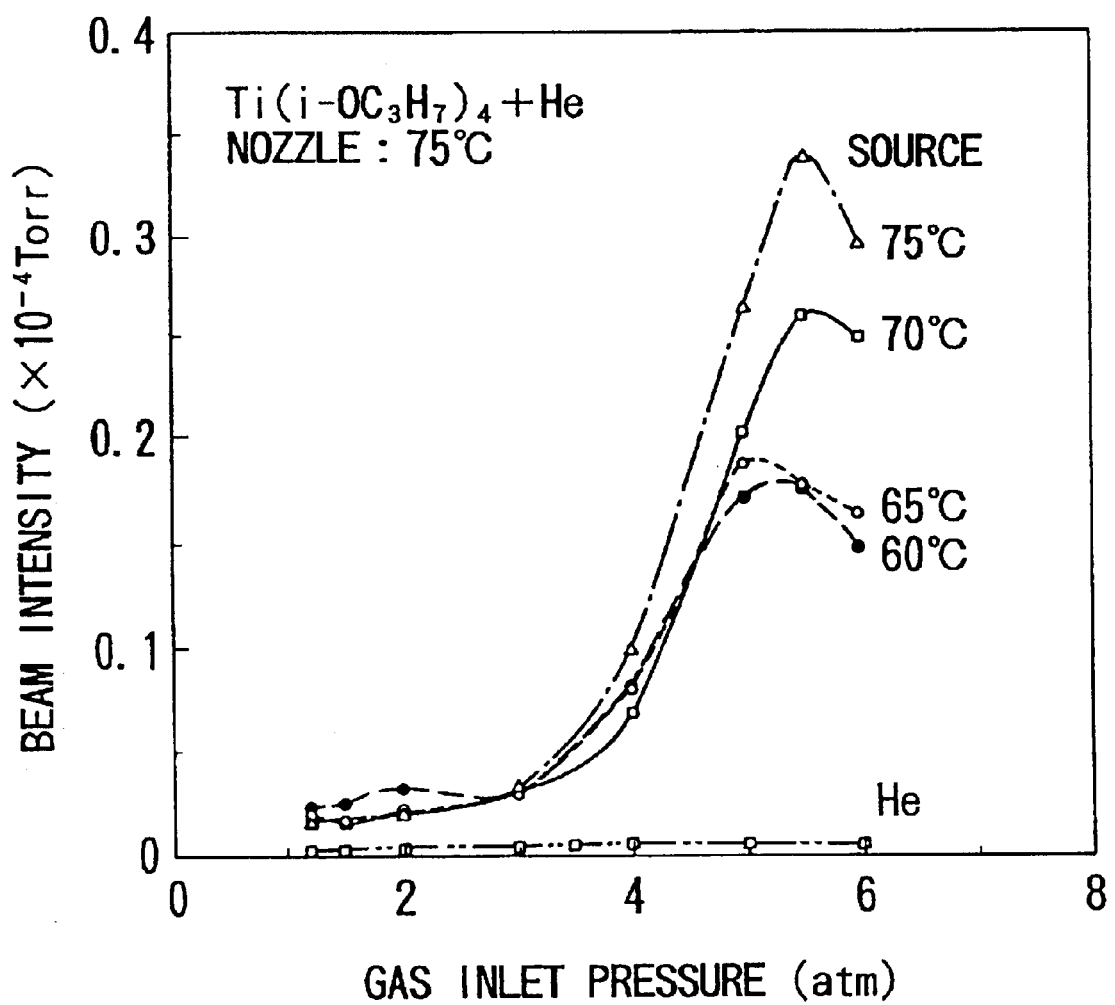
FIG. 3 shows a graph illustrating the He supply pressure dependency of the cluster beam intensity at a Ti(i-OC$_3$H$_7$)$_4$ temperature of from 60 to 75° C.

FIG. 3 illustrates dependency on He supply pressure of the beam intensity of gas cluster of tetra-isopropoxytitanium by using a $Ti(i-OC_3H_7)_4$ mixed gas when causing the raw material temperature to vary between 60 and 75° C. Results of supply of He gas alone are also shown. Temperature of the transport piping and the nozzle was set at 75° C. Beam intensity was measured as a degree of vacuum by providing a vacuum gauge on the beam axis. In this case, generation of a cluster causes a sudden increase in the number of molecules coming into the vacuum gauge, resulting in a lower degree of vacuum. Generation of the cluster was confirmed in accordance with this principle. In the case of He gas alone, no increase in the beam intensity was observed along with the increase in the supply pressure, thus suggesting that no cluster was generated. In the case of a mixed gas, a steep rise of beam intensity is observed under a supply pressure of over 3 atm. This result clearly indicates that $Ti(i-OC_3H_7)_4$ was clusterized.

EXAMPLE 2

Figure 4:
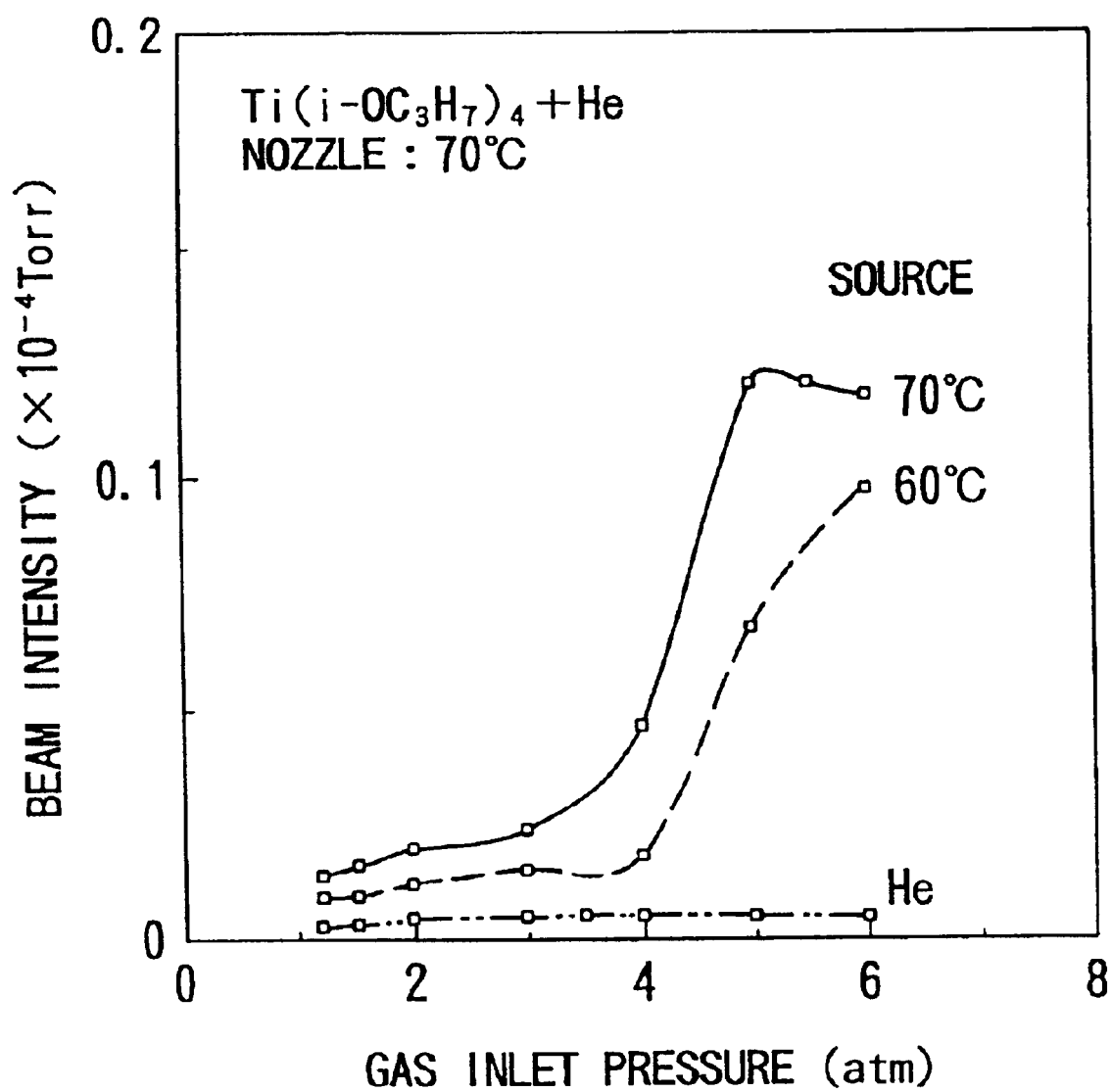
FIG. 4 shows a graph illustrating the He supply pressure dependency of the cluster beam intensity at Ti(i-OC$_3$H$_7$)$_4$ temperatures of 60° C. and 70° C.

FIG. 4 shows dependency on He supply pressure of a $Ti(i-OC_3H_7)_4$ and He mixed gas beam intensity in the case with raw material temperatures of 60° C. and 70° C., and a temperature of the transport piping and the nozzle of 70° C. in Example 1. This similarly suggests that the $Ti(i-OC_3H_7)_4$ gas was clusterized. Beam intensity showed a value lower than in the case with a temperature of the transport piping and the nozzle of 75° C.

Figure 5:
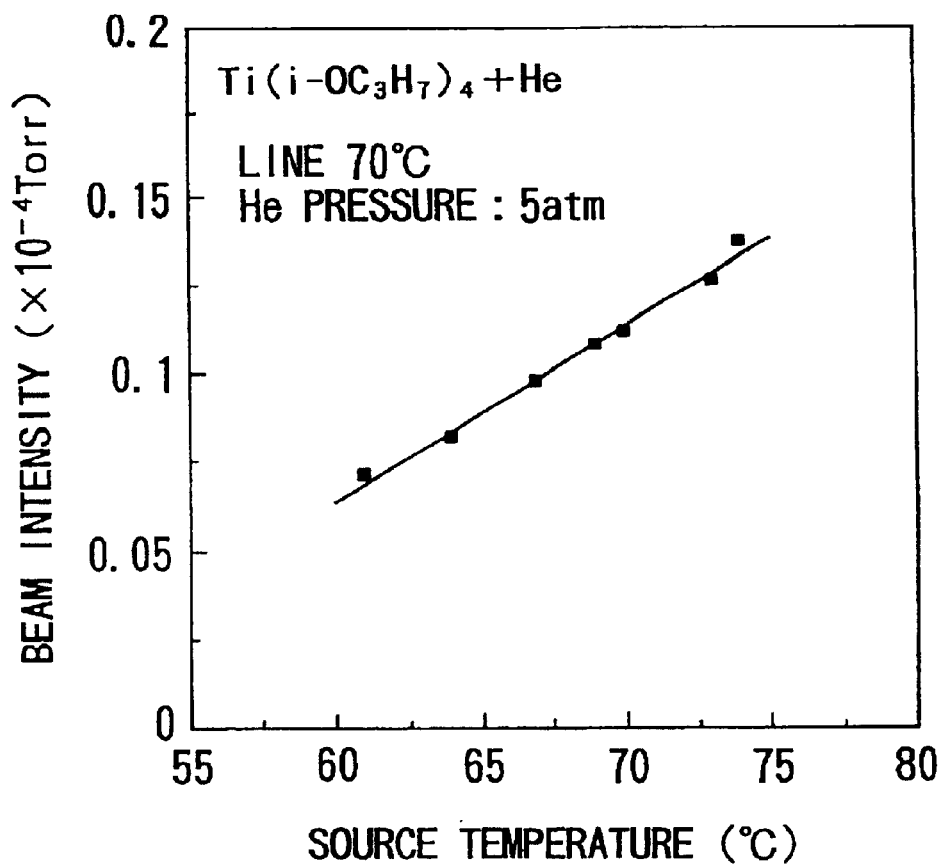
FIG. 5 shows a graph illustrating the relationship between the Ti(i-OC$_3$H$_7$)$_4$ temperature and the beam intensity at a partial pressure of 5 of He.

FIG. 5 illustrates the relationship between the source temperature and the cluster beam intensity under the He gas supply pressure of 5 atm in the case with a temperature of the transport piping and the nozzle of 70° C. Increase in the source temperature leads to a steady increase in the beam intensity.

These generated clusters can be ionized by the application of the electron impact technique or the like. Other materials such as $Zr(t-OC_4H_9)_4$ can also be clusterized.

EXAMPLE 3

Figure 6:
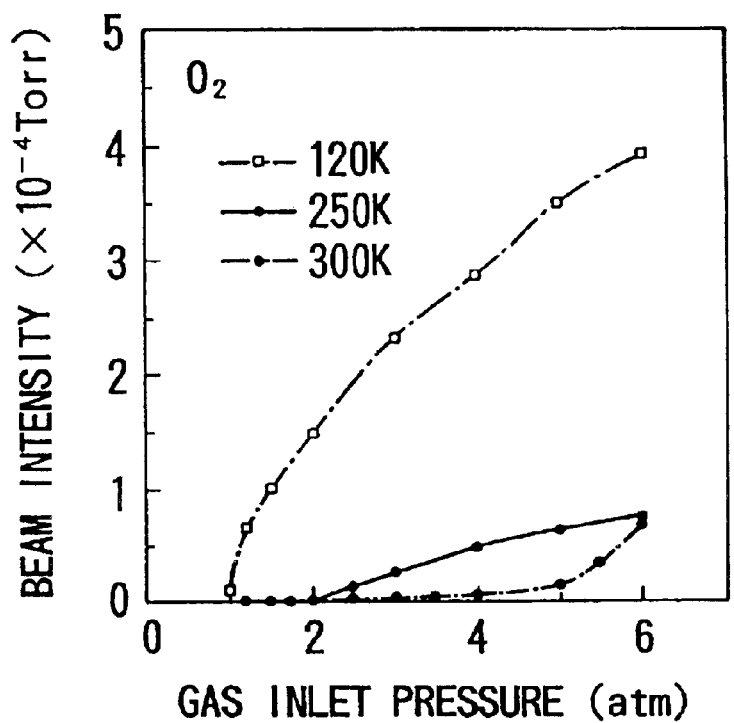
FIG. 6 shows a graph illustrating the supply pressure dependency of the O$_2$ cluster beam intensity whey at various nozzle temperatures.

FIG. 6 illustrates the supply pressure dependency of beam intensity of $O_2$ gas cluster when the nozzle temperature of $O_2$ gas varied between the room temperature and 120 K. While beam intensity shows only a low value as $0.6\times10^{-4}$ Torr at the room temperature under 6 atm, it increases and an increase in cluster beam intensity is observed according as the nozzle is cooled. The $O_2$ gas cluster showed a beam intensity of $4\times10^{-4}$ Torr at 120 K under 6 atm, or an intensity about six times as high as that at the room temperature. Generation of a cluster by nozzle cooling was achieved under a lower supply pressure. This is useful from the point of view of enlarging the cluster size and improvement of background degree of vacuum resulting from a decrease in flow rate.

EXAMPLE 4

Figure 7:
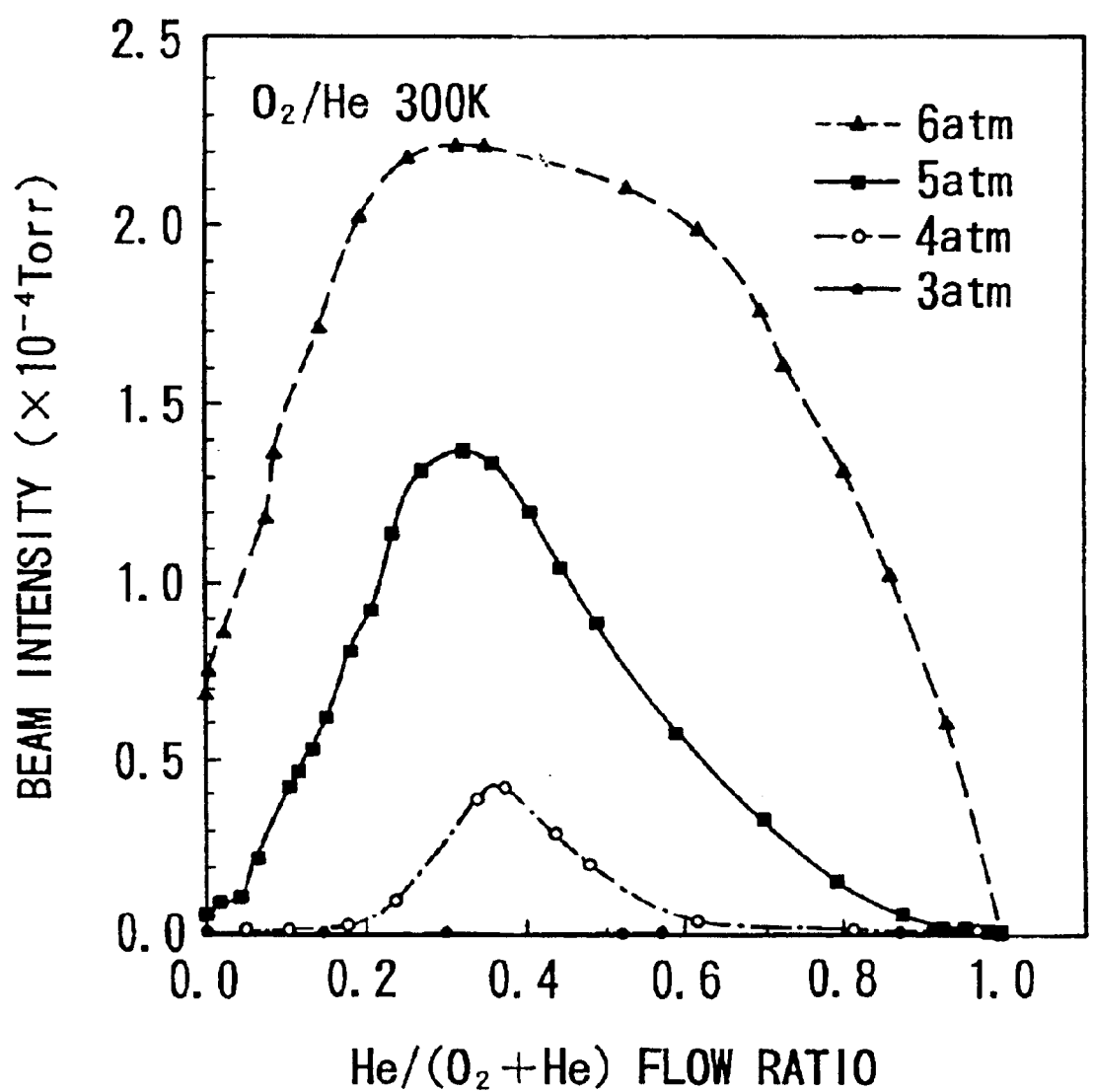
FIG. 7 shows a graph illustrating the relationship between the O$_2$/He mixing ratio and the cluster beam intensity at a nozzle temperature of 300 K.

FIG. 7 shows the dependency on mixing ratio of the neutral beam intensity of an $O_2$/He mixed gas at a nozzle temperature of 300 K. Under any of the supply pressures, an increase in the cluster strength is observed by setting the mixing ratio of He gas to about 30%. Under an He supply pressure of 6 atm, the beam intensity shows, under the effect of mixing of He, a value three times as high as that in the case of $O_2$ gas.

EXAMPLE 5

Figure 8:
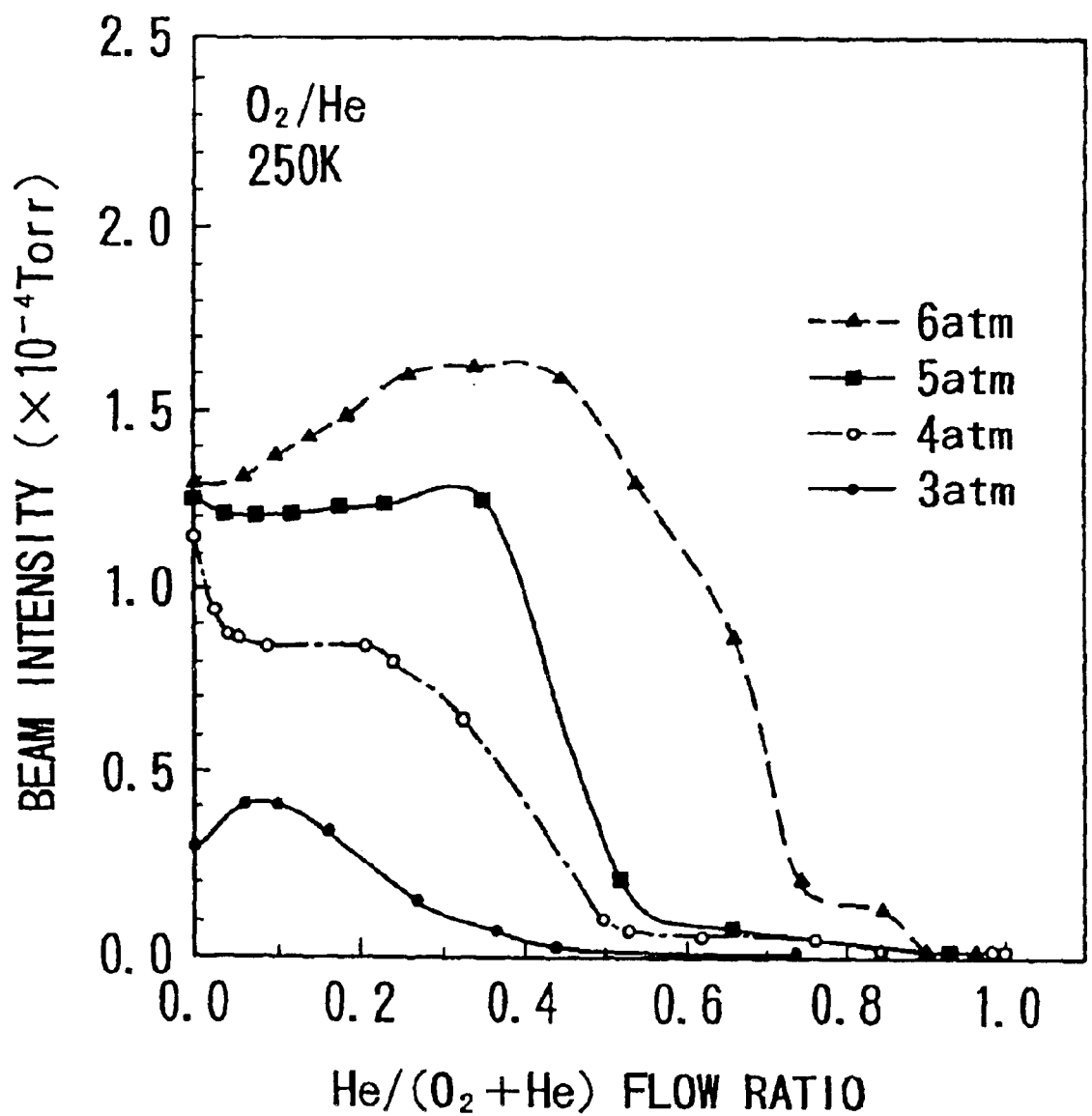
FIG. 8 shows a graph illustrating the case with a nozzle temperature of 250 K corresponding to FIG. 7.
Figure 9:
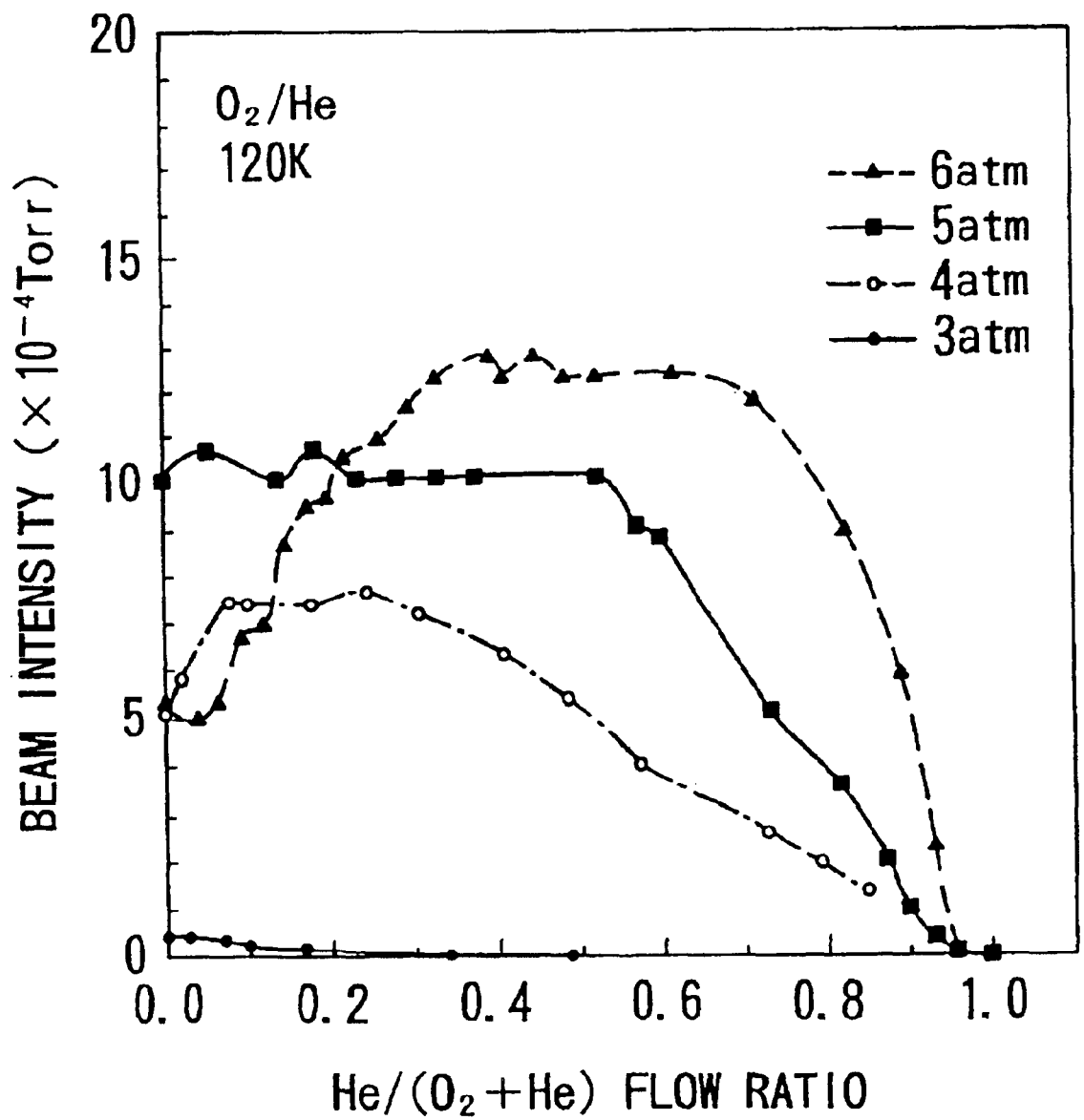
FIG. 9 shows a graph illustrating the case with a nozzle temperature of 120 K corresponding to FIG. 7.

FIGS. 8 and 9 show the dependency on the mixing ratio of $O_2$ gas cluster beam intensity in an $O_2$/He mixed gas when the nozzle temperature was reduced to 250 K and 120

K, respectively. In all cases, mixing of He increased the beam intensity. The case where the nozzle was cooled to 120 K and an He mixing ratio was appropriately selected showed, as compared with the case at a nozzle temperature of 300 K and using $O_2$ gas only, a beam intensity 20 times as high as that under a supply pressure of 6 atm and 80 times as high as that under 5 atm. The maximum beam intensity was $12 \times 10^{-4}$ Torr.

In view of the results presented above, the neutral cluster beam intensity of $O_2$ gas could largely be increased through nozzle cooling and mixing of He by using conditions including a supply pressure of 5 atm, a nozzle temperature of 120 K and an He mixing ratio of about 50%. For $O_2$ cluster, cooling to 120 K gave a six times as high cluster beam intensity, He dilution, a three times as high, and a combination of these two methods, a 20 times as high.

EXAMPLE 6

Figure 10:
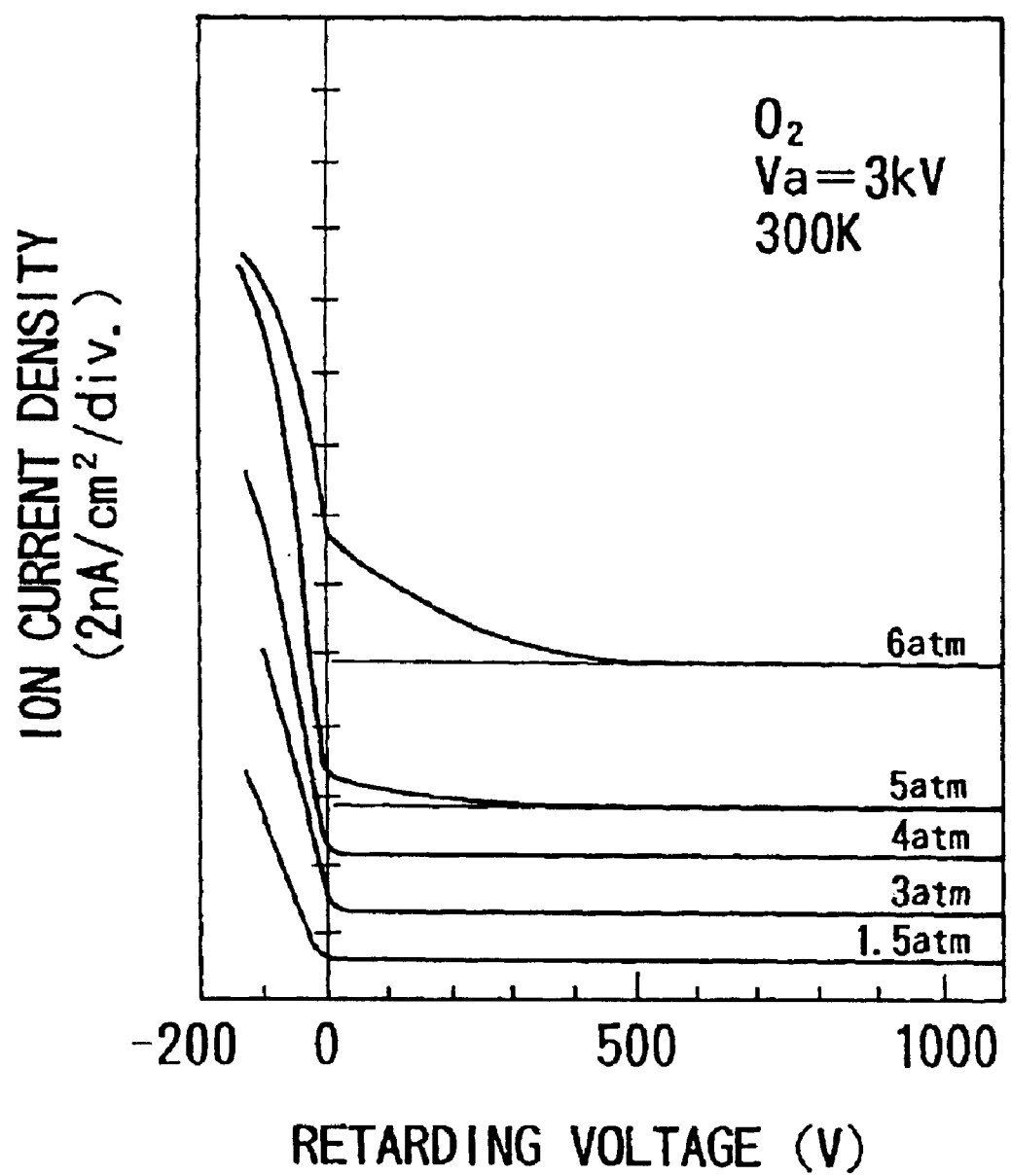
FIG. 10 shows a graph of retarding field spectrum of O$_2$ ion under various supply pressures at a nozzle temperature of 300 K.

FIG. 10 illustrates the retarding field spectrum of $O_2$ cluster ion beam in the case where a nozzle temperature of 300 K was selected and the supply pressure was varied upon ionization through irradiation of electron. Even in a positive retarding field under a supply pressure of over 5 atm, ion current was observed, suggesting the generation of $O_2$ cluster ion beam.

Figure 11:
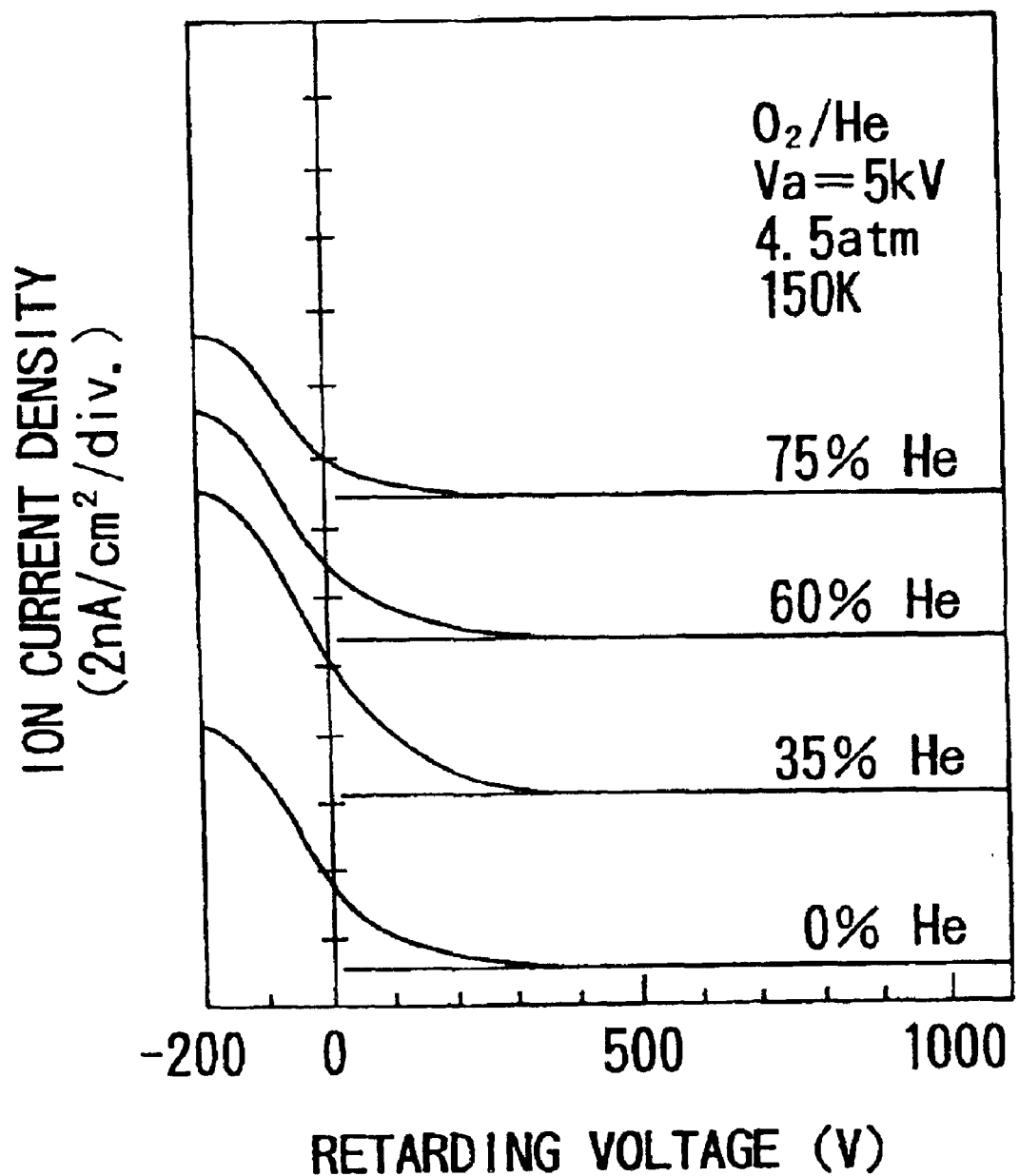
FIG. 11 shows a graph of retarding field spectrum of O$_2$ ion at various He mixing ratios at a nozzle temperature of 150 K.

FIG. 11 shows the retarding field spectrum of $O_2$ ion at various levels of He mixing ratio. Conditions included a gas supply pressure of 4.5 atm, an acceleration voltage of 5 kV, and a nozzle temperature of 150 K. While the case without mixing of He showed a cluster current density of 2.2 $nA/cm^2$, He mixing of 35% gave a current density of 3.9 $nA/cm^2$, or a cluster current 1.8 times as high.

EXAMPLE 7

Figure 12:
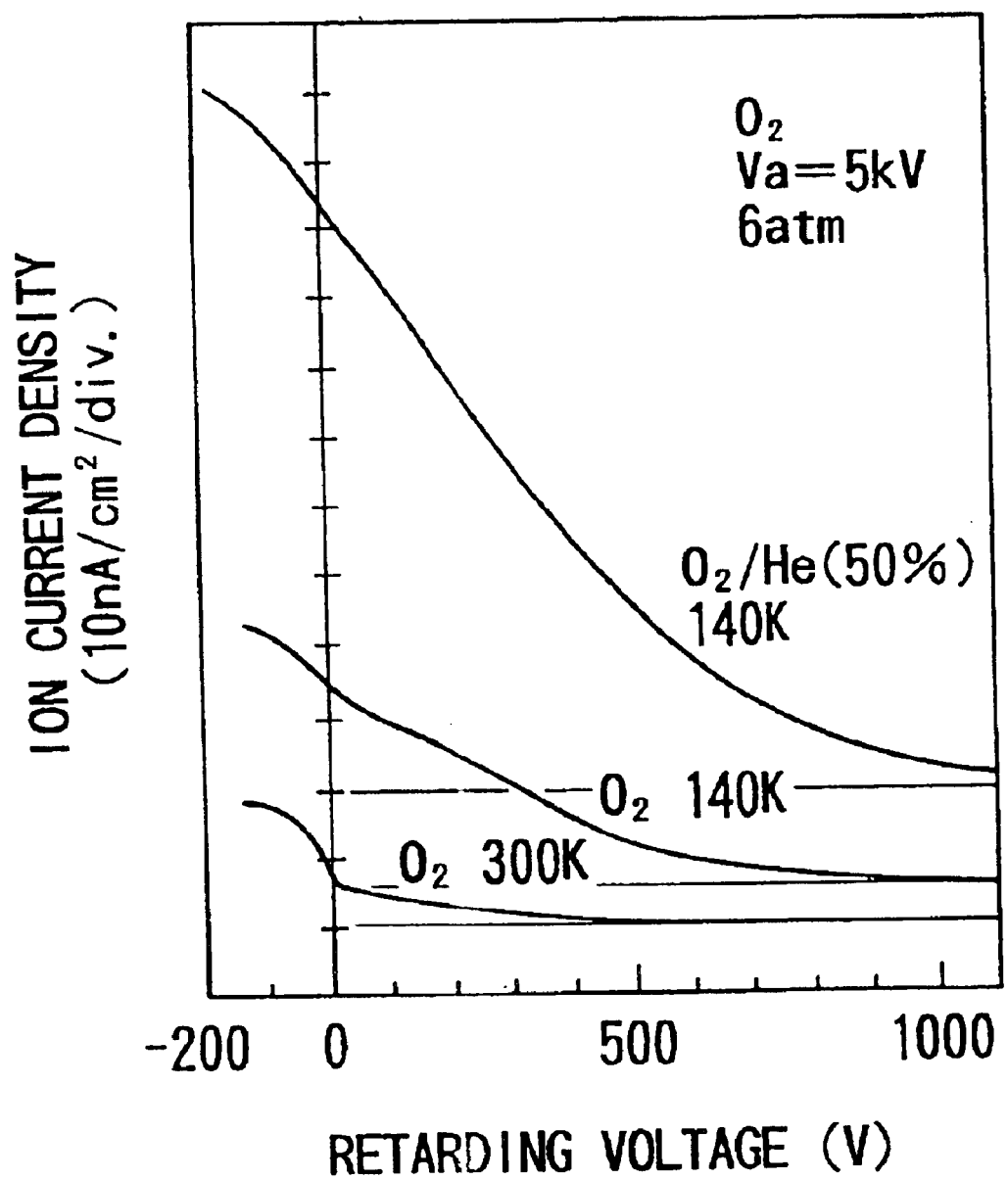
FIG. 12 shows a graph of retarding field spectra of O$_2$ ion at a nozzle temperature of 300 K, when decreasing the nozzle temperature to 140 K, and under conditions including a nozzle temperature of 140 K and 59% mixing of He gas.

FIG. 12 shows the retarding field spectrum of $O_2$ ion in the case where the nozzle temperature was decreased from 300 K to 140 K, and also in the case where He gas was mixed in an amount of 50% with a nozzle temperature of 140 K. The current density of cluster ion was increased to 26 $nA/cm^2$ by nozzle cooling, and to 80 $nA/cm^2$ by mixing of 50% He gas. This current value is 16 times as high as the value at the room temperature.

EXAMPLE 8

Figure 13:
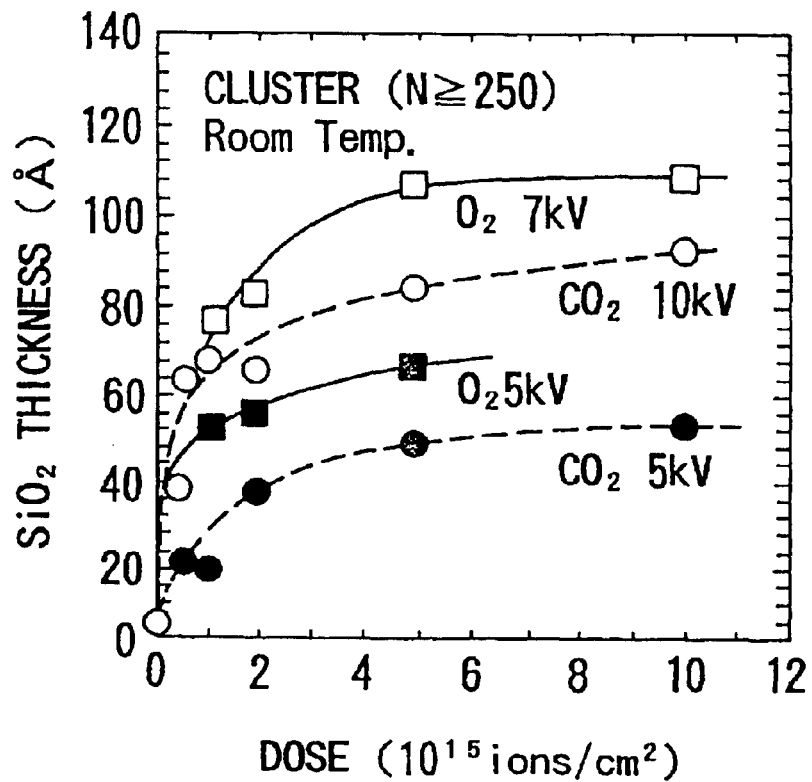
FIG. 13 shows a graph illustrating the dose dependency of the thickness of SiO$_2$ films formed through irradiation of O$_2$ and CO$_2$ cluster ions.

FIG. 13 shows the result of XPS investigation of the film thickness of an oxide film formed by irradiating $O_2$ gas cluster ion formed by mixing 50% He and cooling the nozzle to 140 K onto an Si(100) substrate at the room temperature, together with the result obtained by using $CO_2$ gas. These results suggest formation of an $SiO_2$ film thinner than 11 nm by the irradiation of cluster ions. The oxide film thickness demonstrates a tendency of being saturated at a dose of over about $5 \times 10^{15}$ ions/$cm^2$. Comparison with a constant acceleration voltage, the oxide film formed by $O_2$ cluster ions has a thickness larger than in the case of $CO_2$ cluster and has a higher reactivity.

Figure 14:
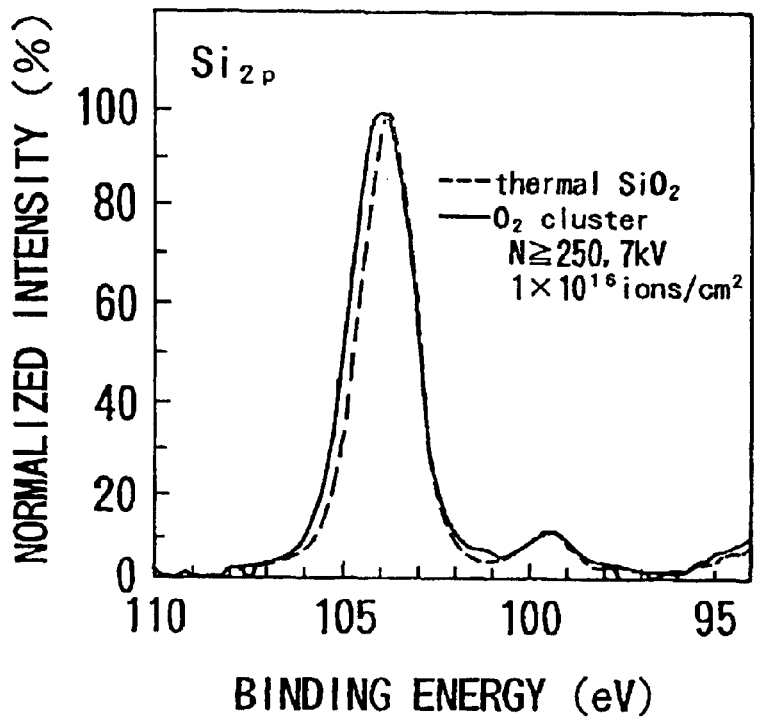
FIG. 14 shows an XPS spectral diagram of an oxide film formed through O$_2$ cluster irradiation.

FIG. 14 illustrates an XPS spectrum of an $SiO_2$ film formed at the room temperature by irradiating 7 keV $O_2$ cluster ions in an amount of $10^{15}$ ions/$cm^2$, together with a spectrum of an $SiO_2$ film formed at 900° C. by the application of the thermal oxidation method commonly used in the LSI manufacturing process. These spectra reveals that the oxide film of a sample formed by the use of $O_2$ clusters has a film structure identical with that of a sample formed by the thermal oxidation method, and a high-quality $SiO_2$ thin film is formed even by the irradiation at the room temperature.

Figure 15:
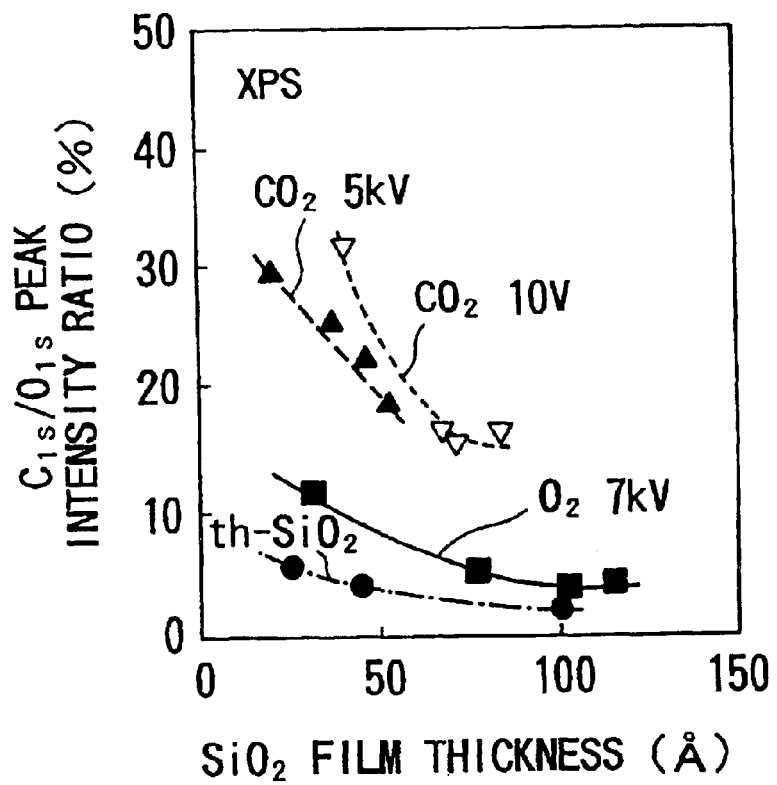
FIG. 15 shows a graph illustrating the carbon concentration in an oxide film.

FIG. 15 shows the carbon concentration in an $SiO_2$ film formed by the use of $O_2$ cluster ion beam in the form of the relationship between the oxide film thickness and the ratio of spectral intensity caused by oxygen and carbon. For comparison purposes, values for an oxide film formed by the use of $CO_2$ cluster ions and a thermal oxide film are also shown. Because carbon is not contained in the thermal oxide film to an extent detectable by the XPS method, these signals are attributable to organic carbon adhering to the surface after formation of the film (detection limit of measurement). The carbon concentration in the oxide film formed by the use of $O_2$ clusters was reduced to below a third that in the case with $CO_2$, thus demonstrating that a lower carbon concentration was successfully achieved.

EXAMPLE 9

Figure 16:
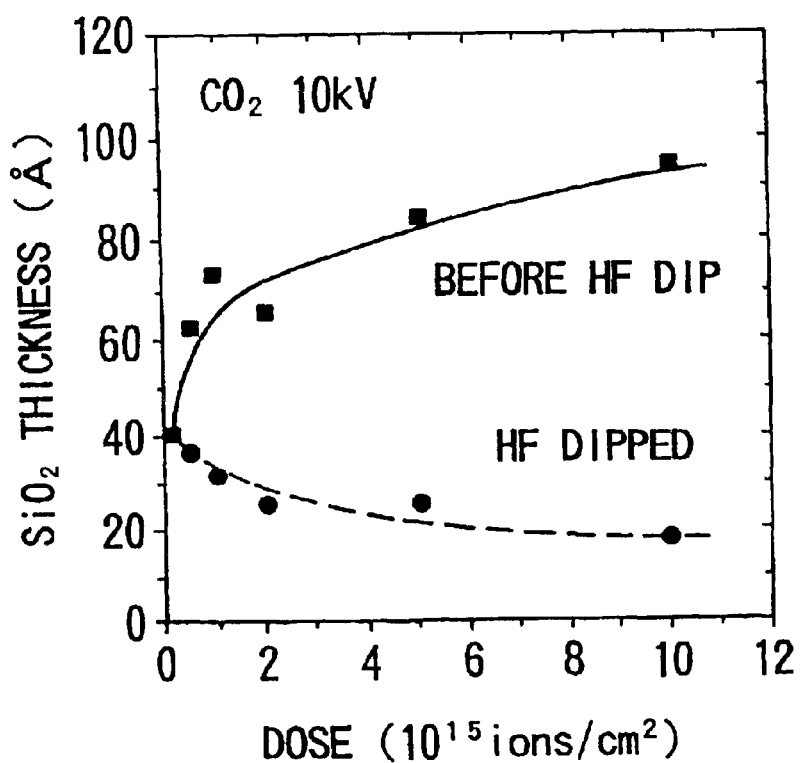
FIG. 16 shows a graph illustrating the thickness of an SiO$_2$ film as determined from an XPS analysis carried out before and after an HF treatment of an oxide film formed through CO$_2$ cluster irradiation.

FIG. 16 shows the thickness of an $SiO_2$ film as determined from an XPS analysis after fluoric acid treatment of the $SiO_2$ film formed by means of $CO_2$ cluster ion beam. The film thickness does not vary between before and after the fluoric acid treatment with a low dose, so that the oxide film on the substrate surface is not a high-quality $SiO_2$ film. Thereafter, the transition film thickness decreases to 20 Å along with the increase in dose.

Figure 17:
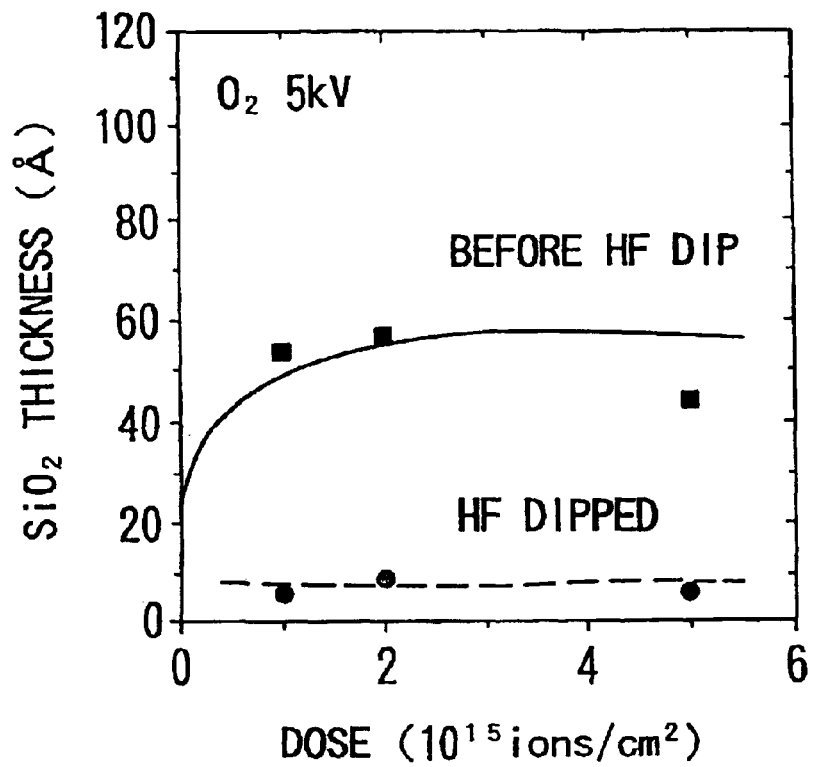
FIG. 17 shows a graph illustrating the thickness of an SiO$_2$ film as determined from an XPS analysis carried out before and after an HF treatment of an oxide film formed through irradiation of 5 keV O$_2$ cluster.
Figure 18:
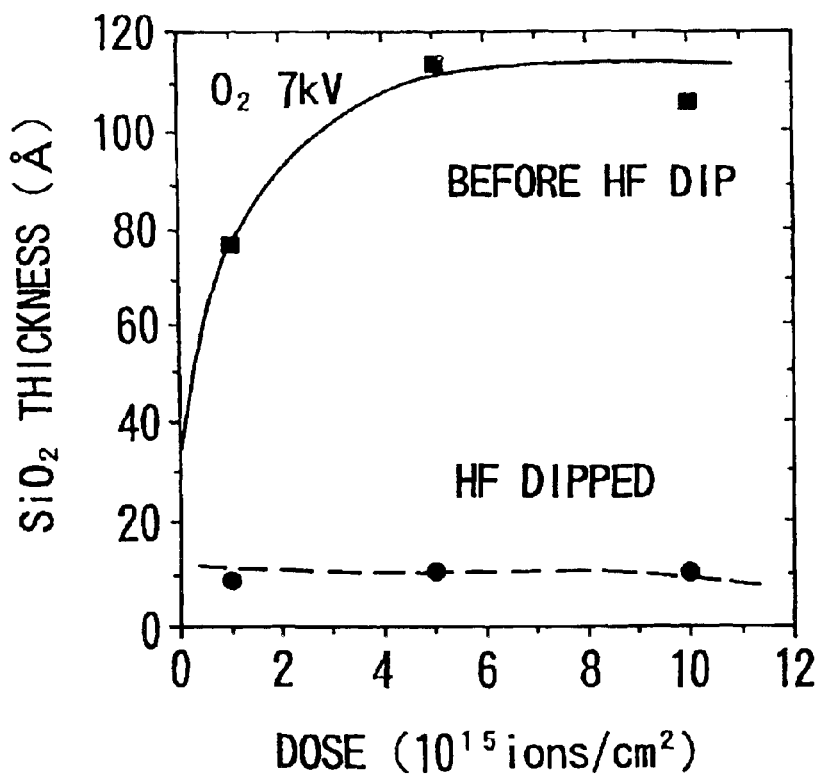
FIG. 18 shows a graph illustrating the thickness of an SiO$_2$ film as determined from an XPS analysis carried out before and after an HF treatment of an oxide film formed through irradiation of 7 KeV O$_2$ cluster.

FIGS. 17 and 18 illustrate the thickness of an $SiO_2$ film as determined by an XPS analysis before and after a fluoric acid treatment of the oxide film formed by irradiating 5 keV and 7 keV $O_2$ cluster ions, respectively. Even with a low ion dose, the oxide film thickness after the fluoric acid treatment is thin as about 10 Å. The oxide film has a better quality as compared with that in the case of $CO_2$ irradiation, thus suggesting that a steep interface was formed between the film and the substrate.

EXAMPLE 10

Figure 19:
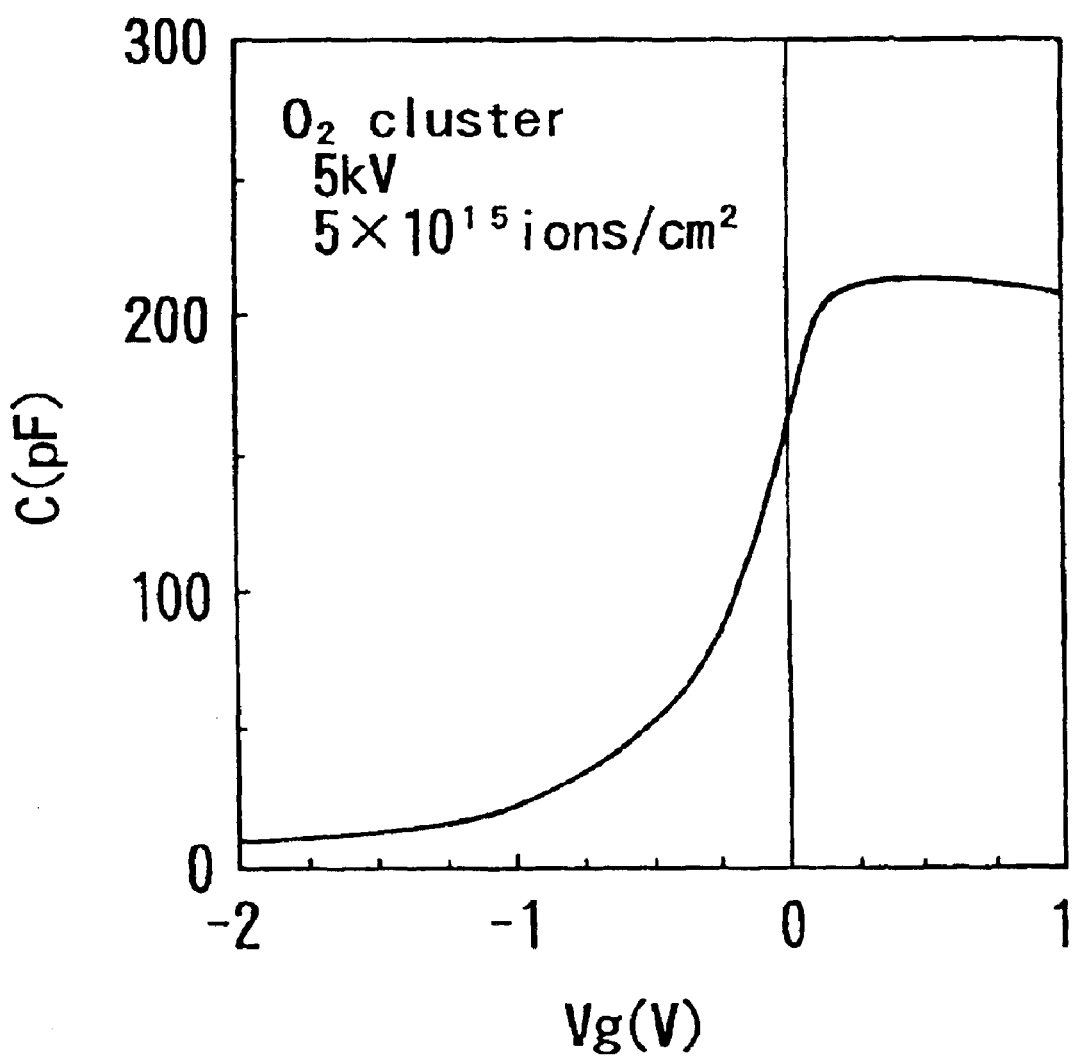
FIG. 19 shows a graph illustrating high-frequency CV characteristics of an MOS capacitor using, as a gate oxide film, an SiO$_2$ film forced through irradiation of O$_2$ cluster ions.

FIG. 19 represents high-frequency CV characteristics of an MOS capacitor using, as a gate insulating film an $SiO_2$ film of 62 Å formed by the use of $O_2$ clusters. The substrate is an n-type Si(100) having a specific resistance of 2 to 3 Ω·cm. Satisfactory C-V characteristics were achieved, indicating that this MOS structure has satisfactory properties as an insulating film for LSI.

EXAMPLE 11

Figure 20:
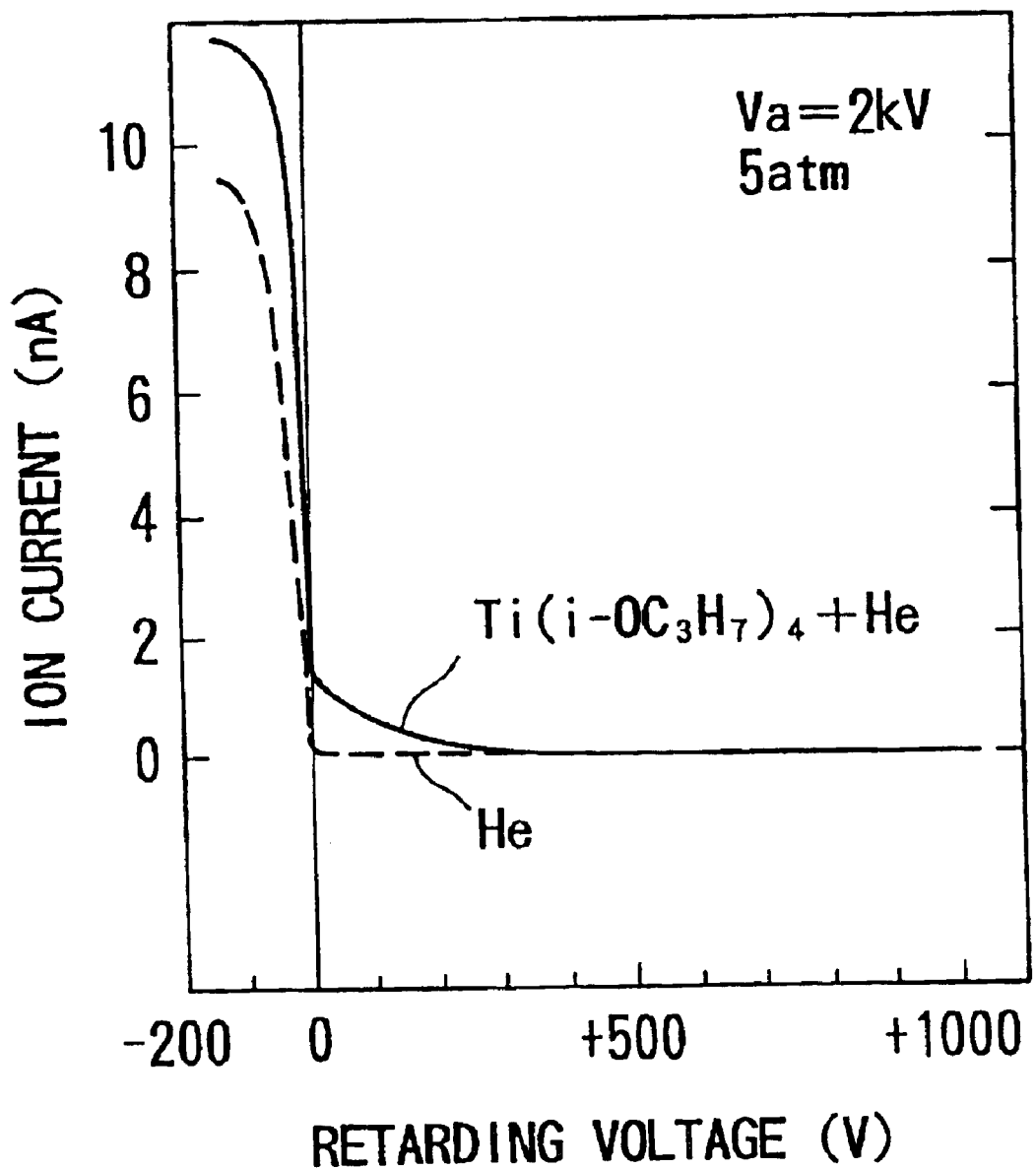
FIG. 20 shows a retarding field spectral diagram after ionization of Ti(i-OC$_3$H$_7$)$_4$/He mixed gas and He gas, respectively.

FIG. 20 shows a retarding field spectrum after ionization of a $Ti(i-OC_3H_7)_4$/He mixed gas and He gas. Conditions included a gas supply pressure of 5 atm, an acceleration voltage of 2 kV, and a nozzle temperature of 75° C. In the case of the $Ti(i-OC_3H_7)_4$/He mixed gas, ion current is observed within a range of retarding voltage of from 0 to 300 V, thus suggesting that $Ti(i-OC_3H_7)_4$ cluster ions have been generated. In this instance, the clusters have an average size of 700 molecules/cluster, and a maximum cluster size of 2,500 molecules/cluster.

EXAMPLE 12

Figure 21:
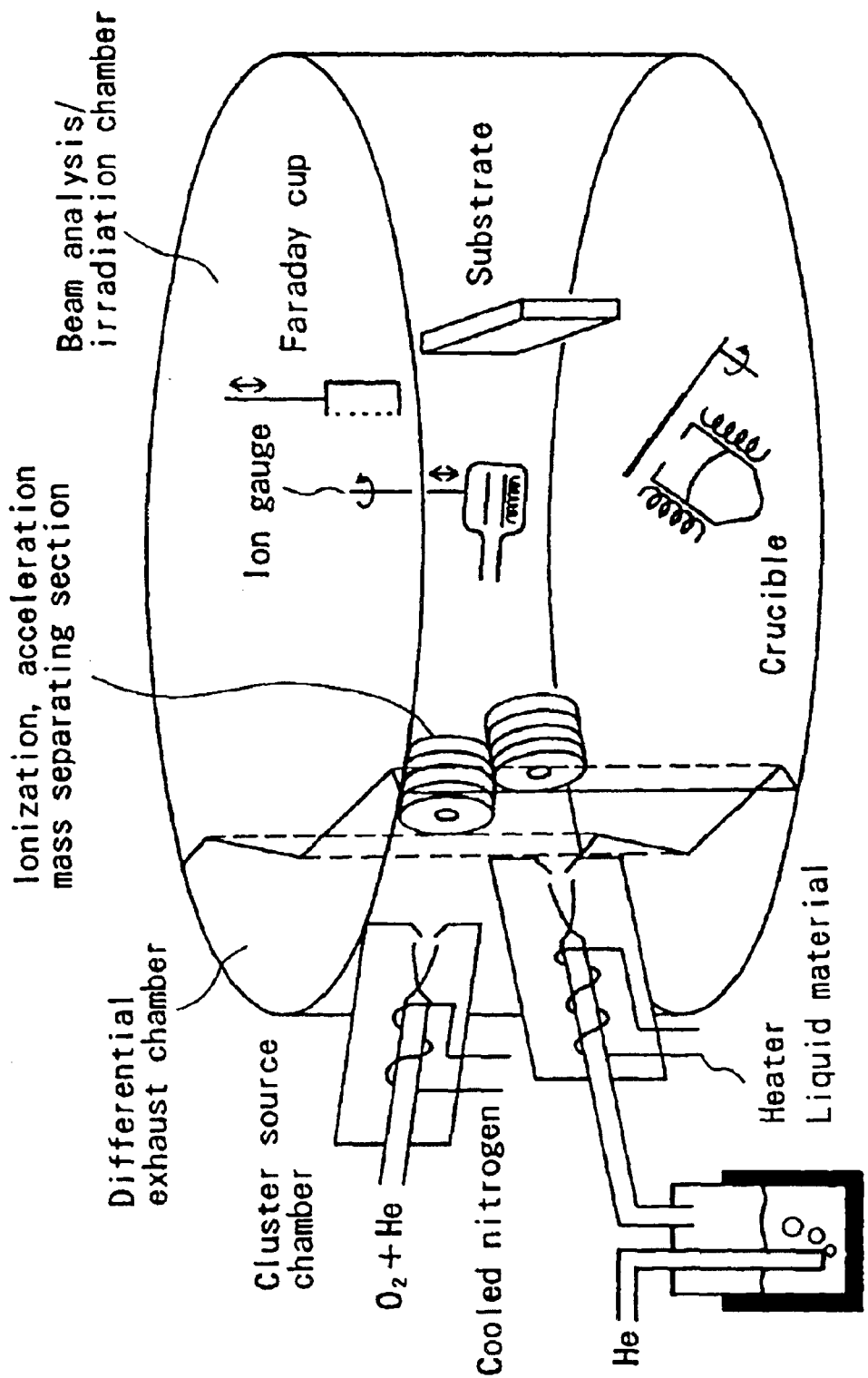
FIG. 21 shows a diagram illustrating an equipment configuration for irradiation for generation of clusters and after ionization thereof.

FIG. 21 illustrates generation of clusters and an outline of the irradiator. A cluster generating section is provided with a nozzle having a rare gas mixing mechanism and a cooling mechanism for generating clusters of oxygen, nitrogen and the like, and a nozzle having a bubbling mechanism for generating clusters of a liquid material. A beam analysis/irradiating chamber is provided with an electrode system for carrying out ionization, acceleration and mass separation, an ion gauge for analyzing a neutral cluster beam, and a Faraday cup for analyzing the size of cluster ions. It is also provided with a substrate holder and an evaporation source for forming a thin film.

EXAMPLE 13

Figure 22:
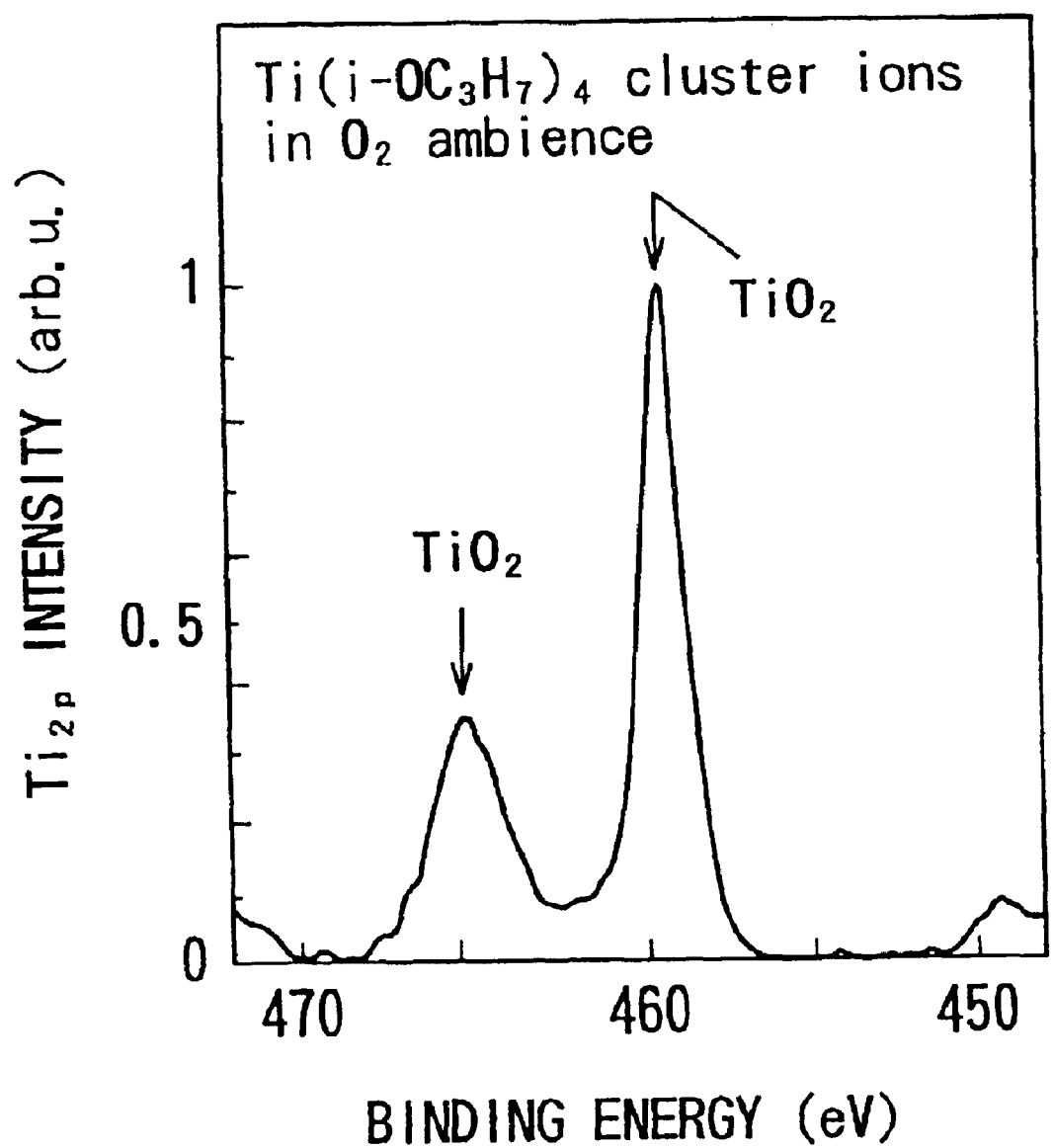
FIG. 22 shows an X-ray photoelectron spectral diagram from Ti2p signal of an Si substrate surface irradiated with Ti(i-OC$_3$H$_7$)$_4$ cluster ions.

FIG. 22 shows an X-ray photoelectron spectrum from a Ti2p signal of an Si substrate surface in the case where $Ti(i-OC_3H_7)_4$ cluster ions accelerated with an acceleration voltage of 7 kV in an oxygen gas atmosphere having an oxygen partial pressure of $3\times10^{-5}$ Torr in the apparatus shown in FIG. 21. The substrate had a temperature of 360° C. Two peaks observed near binding energies of 459 eV and 464 eV are signals from TiO2, suggesting that a TiO2 thin film has been formed. The composition ratio of Ti to 0 as determined from the signal intensity ratio of Ti2p and O21s spectra is 1:2, indicating that a $TiO_2$ thin film satisfying the stoichiometric ratio has been formed.

EXAMPLE 14

Figure 23:
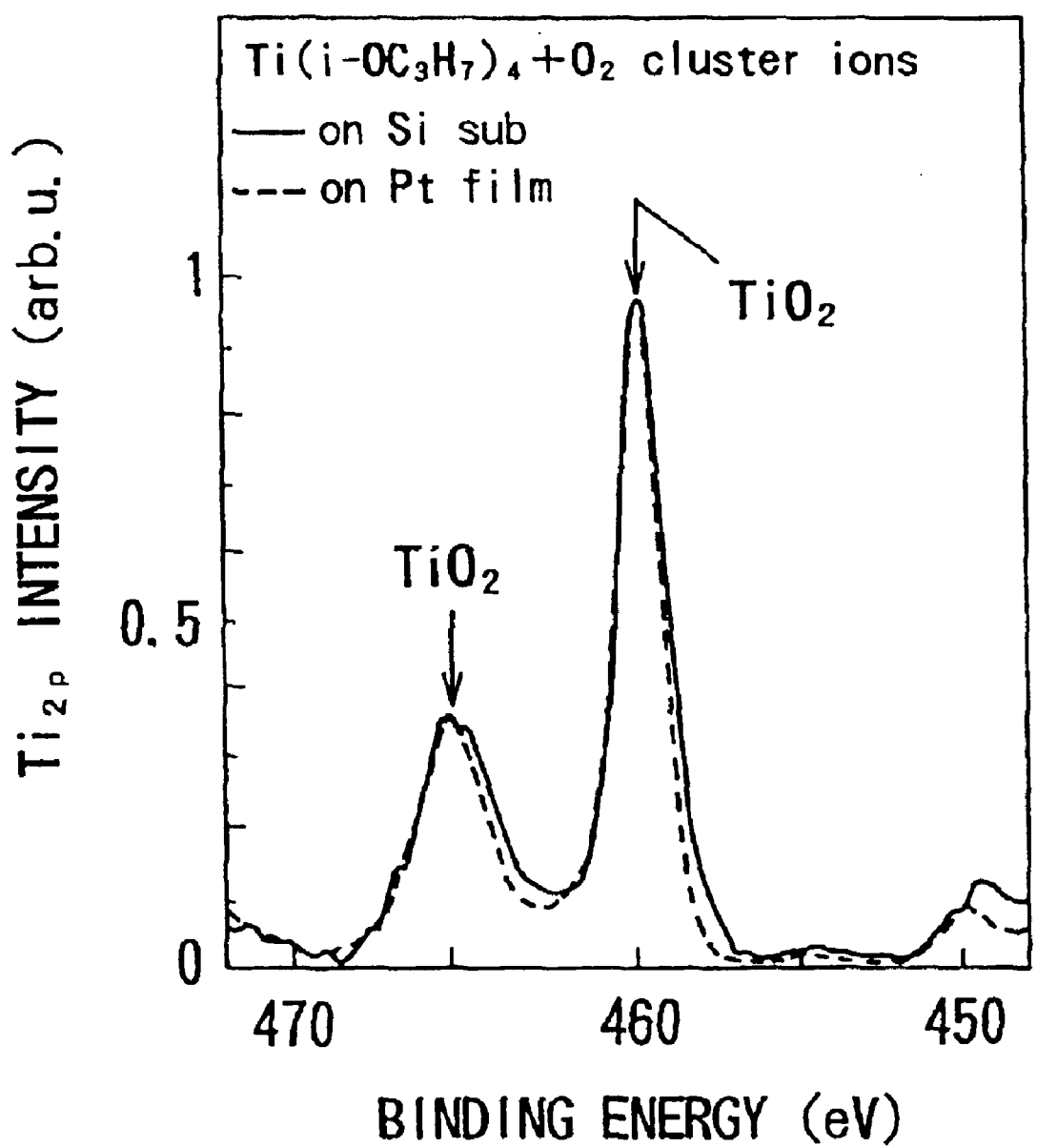
FIG. 23 shows an X-ray photoelectron spectral diagram when irradiating Ti(i-OC$_3$H$_7$)$_4$ vapor and O$_2$ cluster ions.

FIG. 23 illustrates an X-ray photoelectron spectrum of the substrate surface in the case where an Si substrate and a Pt thin film substrate were exposed to $Ti(i-OC_3H_7)_4$ vapor having a partial pressure of $3\times10^{-5}$ Torr, and at the same time, $O_2$ cluster ions accelerated with 7 kV acceleration voltage were irradiated. The substrate had a temperature of 360° C. There are observed $TiO_2$ thin films formed on the both substrates. The composition ratio of Ti to O as determined from the signal intensity ratio of Ti2p and O21s spectra is 1:2, indicating that $TiO_2$ thin films satisfying the stoichiometric ratio have been formed. Also in the case where $TiO(DPM)_2$ was used as a Ti material, a $TiO_2$ thin film satisfying the stoichiometric ratio was formed on the Si substrate, showing the possibility of forming a thin film using various materials by this method.

In addition, $TiO_2$ thin films satisfying the stoichiometric ratio were formed also in the case where $Ti(i-OC_3H_7)_4$ cluster ions accelerated with 7 kV acceleration voltage and $O_2$ cluster ions accelerated with 7 kV acceleration voltage were simultaneously irradiated onto an Si substrate.

EXAMPLE 15

Figure 24:
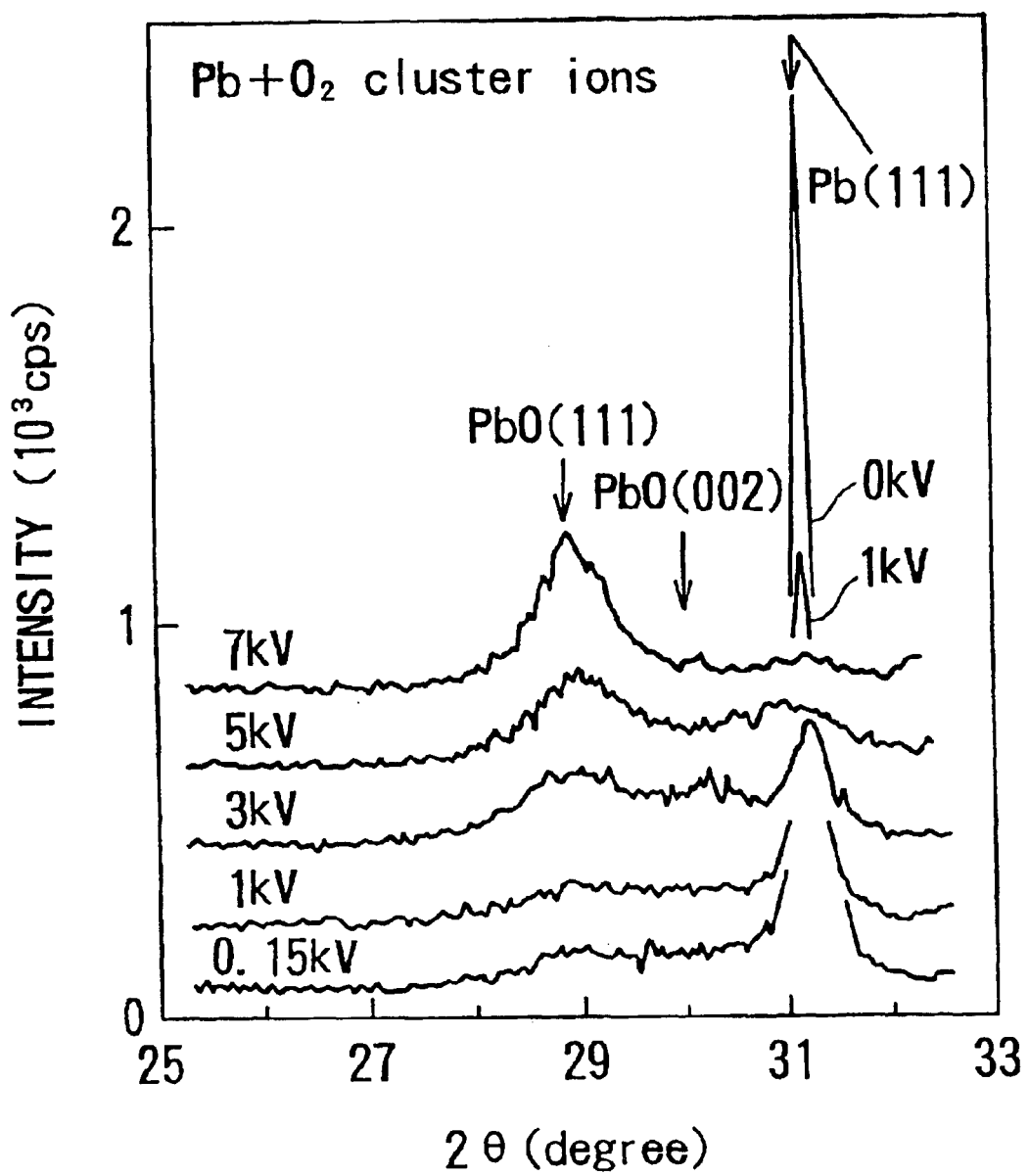
FIG. 24 shows a graph illustrating an X-ray diffraction pattern when irradiating Pb vapor and O$_2$ cluster ions.

FIG. 24 shows an X-ray diffraction pattern of a sample prepared by vapor-depositing Pb by crucible heating at a depositing rate of 0.7 nm/minute onto an $SiO_2$ thin film substrate, and at the same time, irradiating $O_2$ cluster ion beam at different acceleration voltages. The result suggests that a PbO thin film having a preferred (111) orientation was formed by irradiating $O_2$ cluster ion beam with an acceleration voltage of at least 5 kV.

EXAMPLE 16

Figure 25:
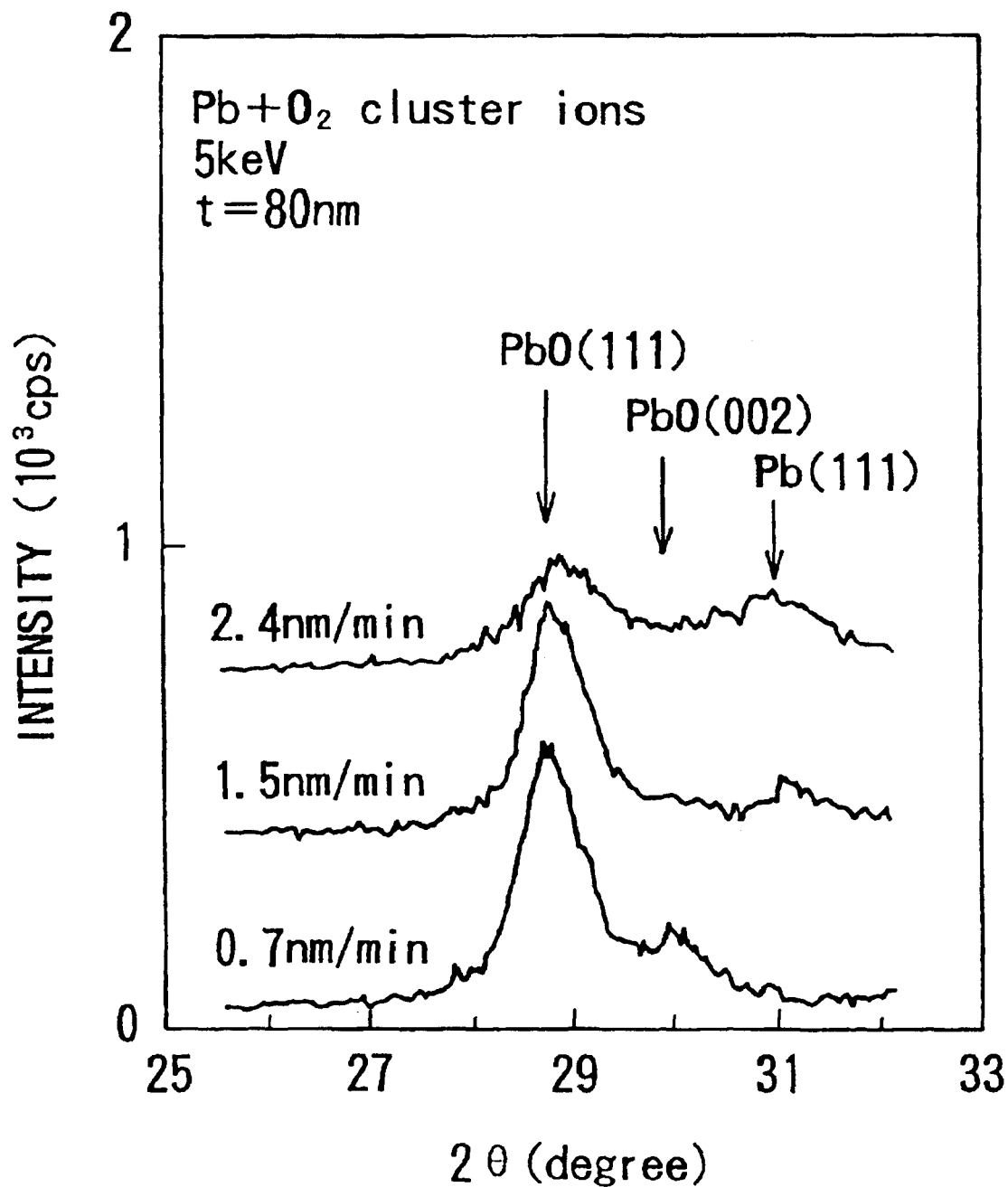
FIG. 25 shows a graph illustrating an X-ray diffraction pattern when irradiating Pb vapor and O$_2$ cluster ions.

FIG. 25 shows an X-ray diffraction pattern of a sample prepared by vapor-depositing Pb onto an $SiO_2$ thin film substrate at various depositing rates, and simultaneously, irradiating $O_2$ cluster ion beam while accelerating with an acceleration voltage of 5 kV. While a PbO thin film was formed in all cases, crystallinity of the PbO thin film is improved by reducing the depositing rate of Pb to below 1.5 nm/minute. In this case, $O_2$ cluster ion beam has a current density of 100 $nA/cm^2$, and crystallinity may be altered by increasing this value.

EXAMPLE 17

Figure 26:
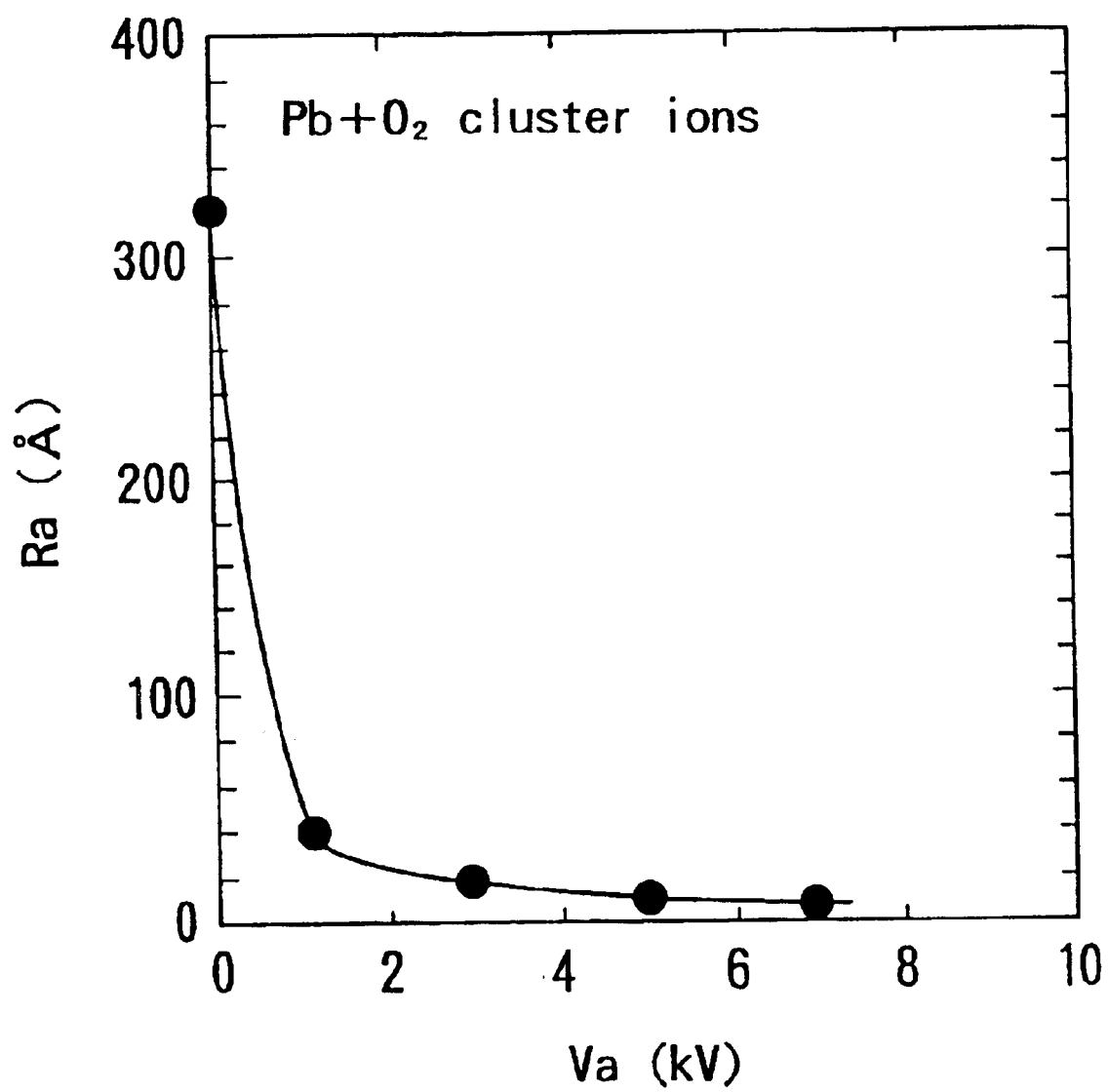
FIG. 26 shows a graph illustrating the average surface roughness (Ra) of a sample when irradiating Pb vapor and O$_2$ cluster ions.

FIG. 26 shows the average surface roughness (Ra) of the surface of a sample prepared by vapor-depositing Pb by crucible heating onto an $SiO_2$ thin film substrate at a depositing rate of 0.7 nm/minute, and at the same time, irradiating $O_2$ cluster ion beam. The surface of the PbO thin film is largely flattened by irradiating $O_2$ cluster ion beam with an acceleration voltage of at least 1 kV. With an acceleration voltage of 7 kV, Ra decreases to 9 Å, and an effect of considerable flattening is obtained.

EXAMPLE 18

Figure 27:
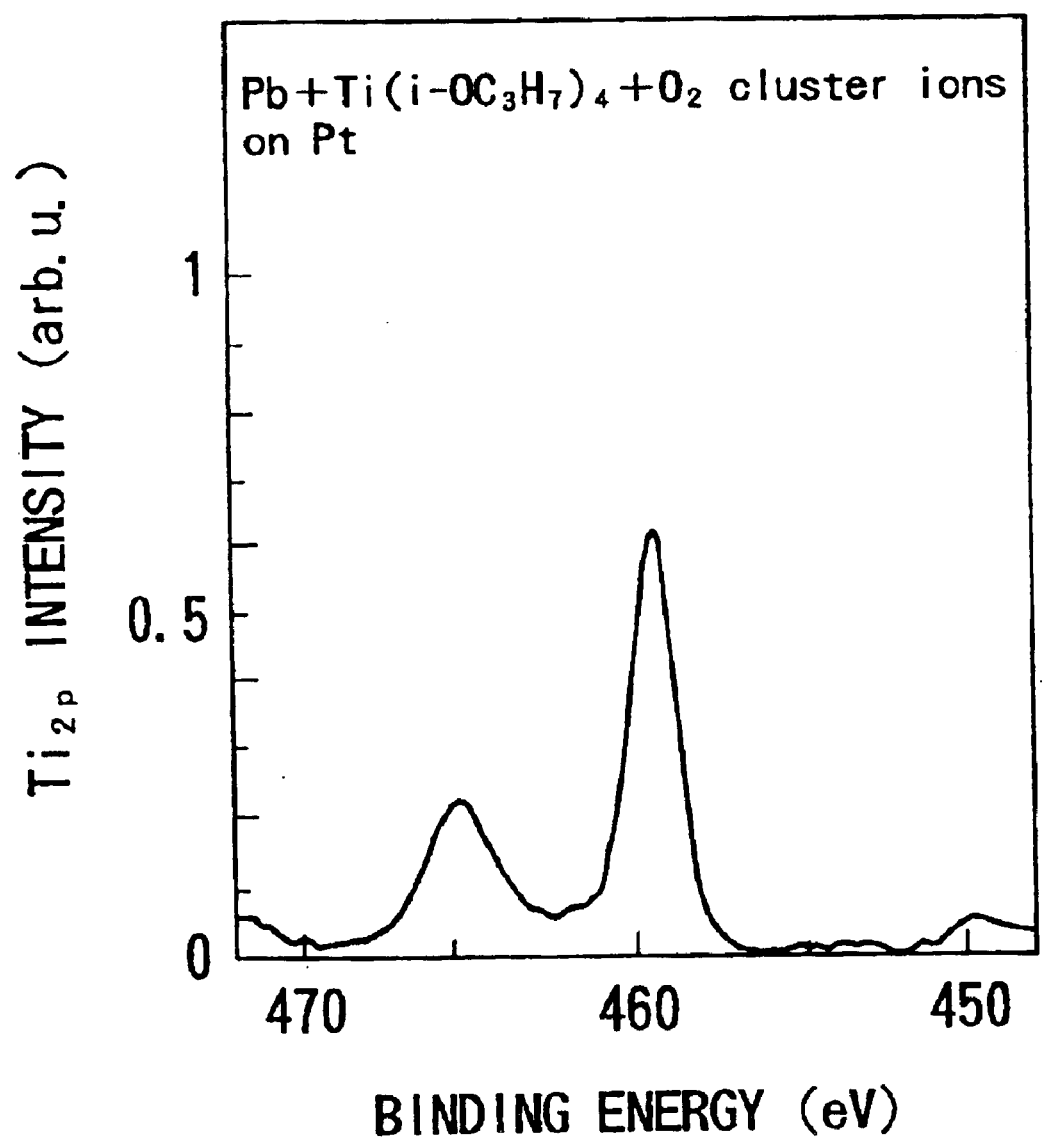
FIG. 27 shows an X-ray photoelectron spectral diagram from Ti2p signal when irradiating Ti(i-OC$_3$H$_7$)$_4$, Pb vapor and O$_2$ cluster ions.

FIG. 27 shows an X-ray photoelectron spectrum from a Ti2p signal of the surface of a sample prepared by exposing a Pt thin film substrate heated to 360° C. to a $Ti(i-OC_3H_7)_4$ atmosphere under a partial pressure of $3\times10^{-5}$ Torr, vapor-depositing Pb at a depositing rate of 0.7 nm/minute, and at the same time, irradiating $O_2$ cluster ion beam accelerated with an acceleration voltage of 7 kV.

Figure 28:
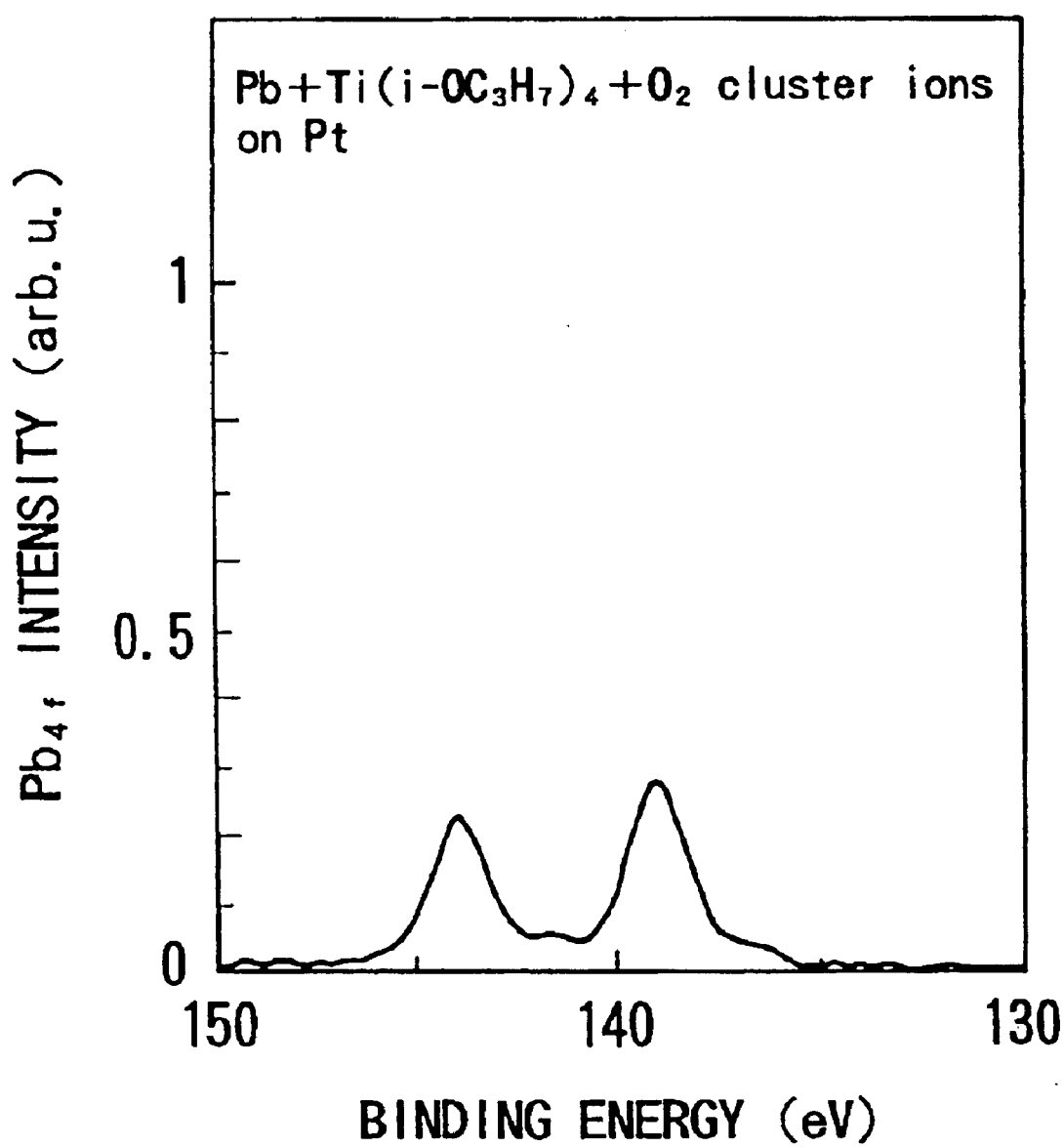
FIG. 28 shows an X-ray photoelectron spectral diagram from Pb4f signal corresponding to FIG. 27.
Figure 29:
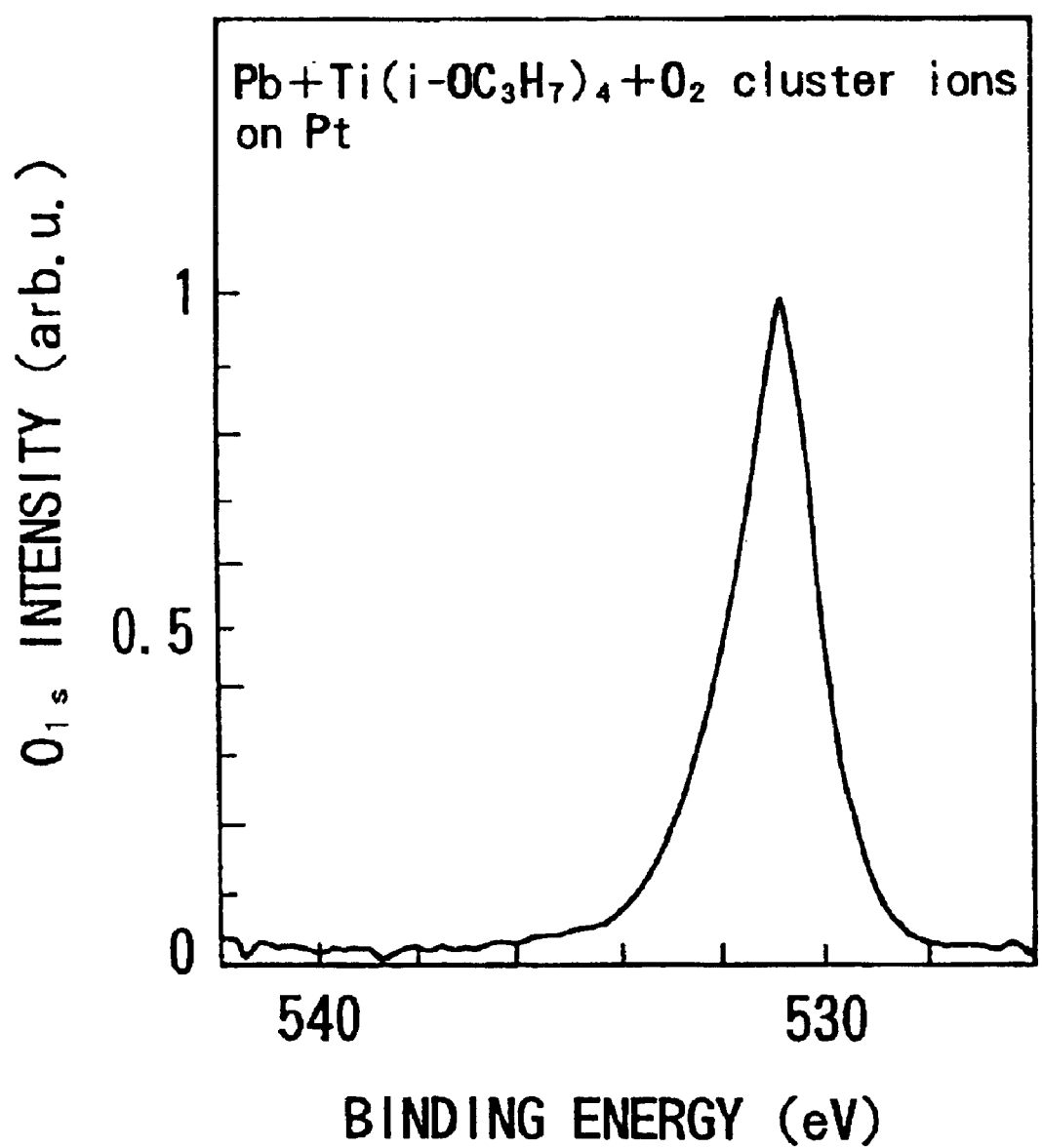
FIG. 29 shows an X-ray photoelectron spectral diagram from O21s signal corresponding to FIGS. 27 and 28.

FIG. 28 illustrates an X-ray photoelectron spectrum from a Pb4f signal of the same sample surface, and FIG. 29, an X-ray photoelectron spectrum from an $O_2$1s signal of the same sample surface. The composition ratio determinable from these X-ray photoelectron spectra of the sample surface is 1:1:3, suggesting that a $PbTiO_3$ ferroelectric thin film satisfying the stoichiometric ratio was formed.

As is clear from this Example, a ferrodielectric thin film was formed by using gas cluster ion beam.

EXAMPLE 19

Figure 30:
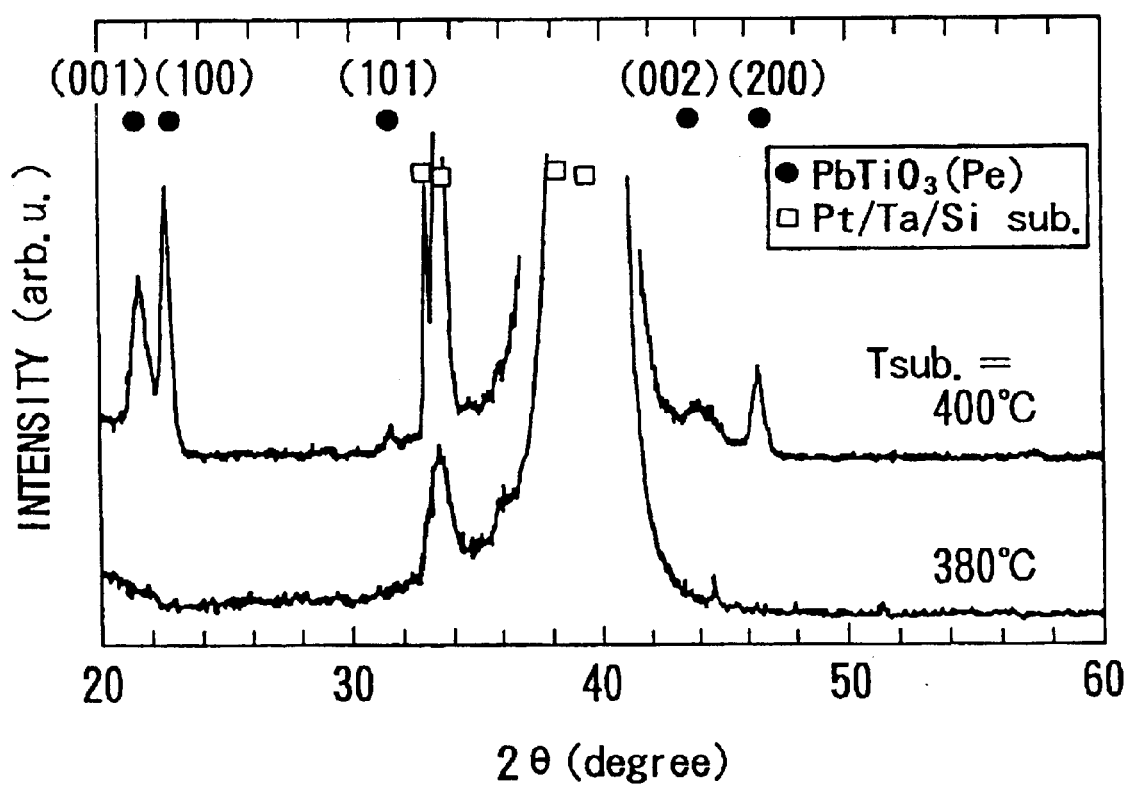
FIG. 30 shows a graph illustrating an X-ray diffraction pattern of a PbTiO3 thin film when irradiating Ti(i-OC$_3$H$_7$)$_4$ thin film when irradiating Ti(i-OC$_3$H$_7$)$_4$, PbO vapor and O$_2$ cluster ions onto a Pt/Ta/Si substrate at substrate temperatures of 400° C. and 380° C.

FIG. 30 shows an X-ray diffraction pattern of a thin film formed by exposing Pt/Ta/Si substrates heated to 400° C. and 380° C. to $Ti(i-OC_3H_7)_4$ atmosphere having a partial pressure of $0.4\times10^{-6}$ Torr, vapor-depositing Pb at a depositing rate of 0.6 nm/minute, and simultaneously, irradiating $O_2$ cluster ion beam having a current density of 100 $nA/cm^2$, accelerated with an acceleration voltage of 7 kV. During vapor deposition, the degree of vacuum was $3\times10^{-5}$ Torr. When using a substrate heated to 400° C., a signal from a $PbTiO_3$ thin film having a perovskite crystalline structure was detected in the X-ray diffraction pattern. A diffraction in (101) orientation is not observed, whereas there are observed (001) and (100) preferential orientations. No diffraction from fixed-dielectric pyrochlore phase is observed in this $PbTiO_3$ thin film. With a substrate temperature of 380° C., the resultant $PbTiO_3$ thin film is non-crystalline. This suggests that a $PbTiO_3$ thin film exhibiting ferroelectricity at a substrate temperature of at least 400° C. This substrate temperature is lower by about 100° C. than that in the application of the CVD method or the sol-gel process. It is known that, when using the CVD method or the sol-gel process, a temperature permitting formation of a fixed dielectric pyrochlore phase exists between the substrate temperature permitting formation of a non-crystalline phase and the temperature permitting formation of the perovskite phase. Formation of a pyrochlore phase is not observed when using gas clusters. It is thus possible to transport oxygen acting as an oxygen source with a high density, form a thin film through surface reaction under a high vacuum, and obtain a high-quality ferroelectric thin film at a low temperature.

EXAMPLE 20

Figure 31:
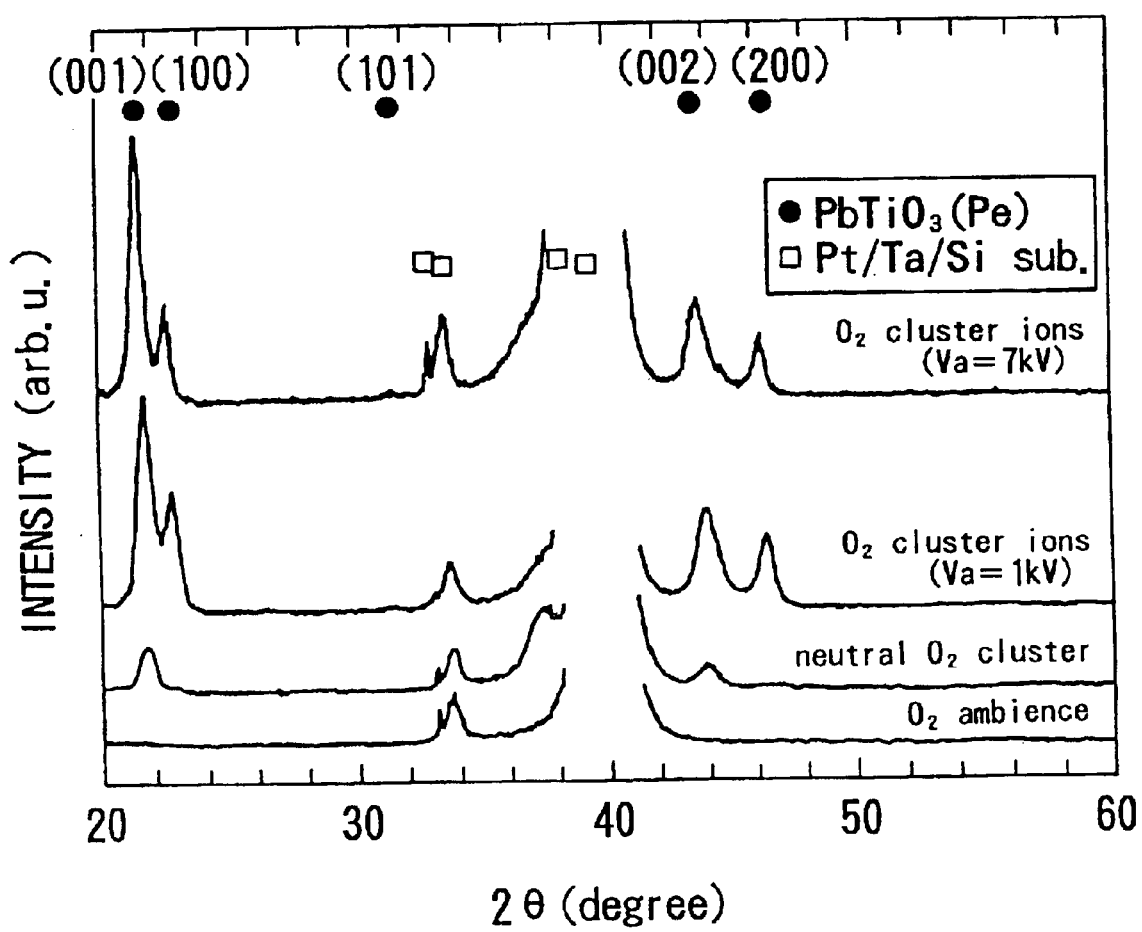
FIG. 31 shows a graph illustrating an X-ray diffraction pattern of a thin film formed by irradiating Ti(i-OC$_3$H$_7$)$_4$, PbO vapor, and various O$_2$ sources onto a Pt/Ta/Si substrate at a substrate temperature of 430° C.

FIG. 31 shows an X-ray diffraction pattern of a thin film formed by exposing $Ti(i-OC_3H_7)_4$ to an atmosphere having a partial pressure of $0.4\times10^{-5}$ Torr on a Pt/Ta/Si substrate heated to 430° C., vapor-depositing PbO at a depositing rate of 0.5 nm/minute, and at the same time, supplying oxygen under various conditions. When supplying oxygen having a partial pressure of $3\times10^{-5}$ Torr as an oxidizing agent, the resultant thin film is non-crystalline. When irradiating neutral $O_2$ clusters not ionized, a single perovskite phase having sa low crystallinity was obtained. Clusters have a kinetic energy cluster size times as high as that in a monomolecular state. Consequently, kinetic energy held by the neutral $O_2$ clusters contributes to crystallization, thus making available perovskite. Crystallinity is largely improved by increasing acceleration voltage for the $O_2$ cluster ions to 1 to 7 kV. Even a low acceleration voltage of 1 kV gave an effect of largely improving crystallinity.

In addition to the Pb and Ti sources as described above, addition of Zr-containing materials and/or La-containing materials makes it possible to form a Pb-based ferroelectric thin film such as $Pb(Zr, Ti)O_3$ and $(Pb, La)(Zr, Ti)O_3$. By using Bi-containing materials, Ti-containing materials and Sr-containing materials as raw materials, it is also possible to form a Bi laminate ferroelectric thin film such as $BiSr_2Ta_2O_9$.

EXAMPLE 21

Figure 32:
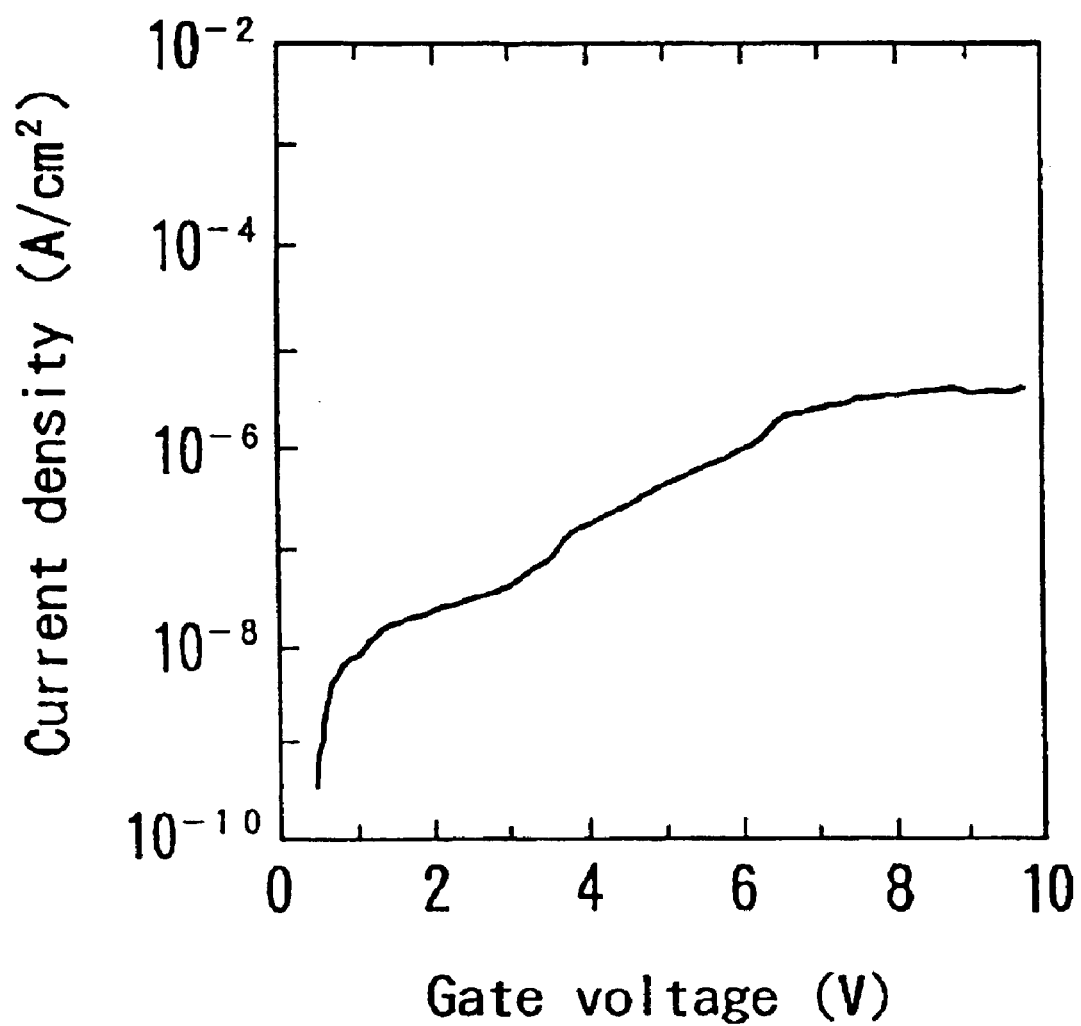
FIG. 32 shows a current-voltage curve of a PbTiO$_3$ thin film obtained by irradiating Ti(i-OC$_3$H$_7$)$_4$, PbO vapor and O$_2$ cluster ion beam onto a Pt/Ta/Si substrate at a substrate temperature of 430° C.

FIG. 32 represents current-voltage characteristics of a capacitor prepared by depositing Au by the sputtering process on an upper portion of a $PbTiO_3$ thin film formed by the method of Example 20 with an acceleration voltage of 3 kV of $O_2$ cluster ions. An applied voltage of 5 V leads to a leak current density of $1\times10^{-6}$ $A/cm^2$, suggesting that a high-quality thin film exhibiting a low leak current is formed. The relationship between field and polarization of the thus formed capacitor shows a hysteresis history, demonstrating that a ferrodielectric thin film having a spontaneous polarization property was formed.

According to the present invention, as described above in detail, it is possible to convert into gas cluster even a substance liquid at the room temperature under the atmospheric pressure, to ionize same, and further, form a thin film thereof. More specifically, according to the present invention, improvements are available including the possibility of accomplishing replenishing of raw materials outside the vacuum unit, and of directing the beam downward irrespective of the gravity, bringing about such effects as increase in cluster size, increase in cluster beam intensity, i.e., the possibility of assisting cooling of $Ti(i-OC_3H_7)_4$ and promoting growth of $Ti(i-OC_3H_7)_4$ clusters under the heat absorbing effect upon release of the carrier gas into vacuum. In addition, because the amount of supplied condensed gas through the amount of supplied carrier gas capable of being precisely controlled, it is possible to stabilize beam intensity. By using a reactive gas such as $O_2$, it is also possible to form clusters comprising a mixture of a liquid material and a gaseous material.

By irradiating cluster ions of a reactive substance such as an oxygen-containing compound onto a substrate surface and causing reaction thereof, it is possible to form various high-quality-thin oxide films and crystalline composite insulating films at a relatively low temperature.

What is claimed is:

1. A method for forming a gas cluster which comprises the steps of mixing a substance liquid at room temperature under atmospheric pressure and a pressurized gas, and causing the resultant mixture to spout as a gas from a nozzle to generate a cluster which is a lumpy group of atoms or molecules.

2. The method as claimed in claim 1, wherein said substance liquid at the room temperature under the atmospheric pressure is an oxygen-containing compound.

3. The method as claimed in claim 1, wherein said substance liquid at the room temperature under the atmospheric pressure is an organic metal compound.

4. The method as claimed in claim 1, wherein said substance liquid at the room temperature under the atmospheric pressure is $Ti(i-OC_3H_7)_4$.

5. The method as claimed in claim 1, wherein said pressurized gas is an inert gas or a reactive gas.

6. The method as claimed in claim 1, wherein said nozzle is an expansion-type nozzle.

7. The method for forming gas cluster ions, which comprises the step of ionizing the gas cluster formed by the method as claimed in claim 1.

8. The method as claimed in claim 7, wherein said ionization is accomplished by irradiating an electron beam.

9. A method for forming a thin film, which comprises the step of irradiating the cluster ions formed by the method as claimed in claim 7 onto a substrate surface, thereby forming a thin film.

10. A method as claimed in claim 9, wherein said cluster ions are accelerated by acceleration voltage.

11. A method for forming a thin film, which comprises the steps of forming a cluster which is a lumpy group of atoms or molecules of a reactive substance gaseous at room temperature, irradiating cluster ions ionized therefrom onto a substrate surface, and at the same time or alternatively, irradiating a plurality of component gases of a deposit film onto the substrate surface to cause reaction thereof, thereby depositing a thin film on the substrate surface;

wherein two or more gases to be irradiated simultaneously are fed after converting same into clusters.

12. A method for forming a thin film as claimed in claim 11, which comprises the steps of irradiating oxygen gas cluster ions onto the substrate, and at the same time, or alternately, irradiating a plurality of component gases of a deposit film onto the substrate surface to cause reaction of both, thereby depositing a thin ferroelectric film on the substrate surface.

13. A method for forming a thin film as claimed in claim 11, wherein an oxide film is deposited by irradiating cluster ions of a gas containing oxygen and at least an organic metal compound gas onto the substrate surface.

14. A method for forming a thin film, which comprises the steps of forming a cluster which is an annular group of atoms or molecules of a reactive substance gaseous at room temperature, irradiating cluster ions ionized therefrom onto a substrate surface, and at the same time or alternatively, irradiating a plurality of component gases of a deposit film onto the substrate surface to cause reaction thereof, thereby depositing a thin film on the substrate surface; wherein at least one of the gaseous reactive substances to be converted into cluster is an oxygen-containing substance.

* * * * *